(12) United States Patent
Dix et al.

(10) Patent No.: US 7,655,758 B2
(45) Date of Patent: *Feb. 2, 2010

(54) STABLE LIQUID IL-1 ANTAGONIST FORMULATIONS

(75) Inventors: Daniel Dix, Langrangeville, NY (US); Katherine Bowers, Clayton, NC (US); Chimanlall Goolcharran, Hopewell Junction, NY (US); Leu-Fen H. Lin, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/048,717

(22) Filed: Mar. 14, 2008

(65) Prior Publication Data
US 2008/0188817 A1    Aug. 7, 2008

Related U.S. Application Data

(63) Continuation-in-part of application No. 11/750,613, filed on May 18, 2007, which is a continuation-in-part of application No. 11/205,935, filed on Aug. 17, 2005, now Pat. No. 7,365,165.

(60) Provisional application No. 60/602,137, filed on Aug. 17, 2004.

(51) Int. Cl.
*A61K 36/20* (2006.01)
*A61K 47/48* (2006.01)
*C07K 14/475* (2006.01)

(52) U.S. Cl. .............................. 530/351; 514/12; 514/2; 424/85.4

(58) Field of Classification Search .................... None
See application file for complete search history.

(56) References Cited

U.S. PATENT DOCUMENTS

| | | | |
|---|---|---|---|
| 5,399,670 | A | 3/1995 | Bhattacharya et al. |
| 6,267,958 | B1 | 7/2001 | Andya et al. |
| 6,410,511 | B2 * | 6/2002 | L'Italien et al. ............... 514/12 |
| 6,875,432 | B2 | 4/2005 | Liu et al. |
| 7,001,892 | B1 | 2/2006 | Chmielewski et al. |
| 7,060,268 | B2 | 6/2006 | Andya et al. |
| 2003/0113316 | A1 | 6/2003 | Kaisheva et al. |
| 2003/0143697 | A1 | 7/2003 | Stahl et al. |
| 2003/0180287 | A1 * | 9/2003 | Gombotz et al. ......... 424/130.1 |
| 2006/0217311 | A1 | 9/2006 | Dix et al. |

FOREIGN PATENT DOCUMENTS

WO    WO93/00807    1/1993

OTHER PUBLICATIONS

Daugherty and MRSNY, 2006, "Formulation and delivery issues for monoclonal antibody therapeutics.", Advanced Drug Delivery Reviews 58: 686-706.
Katayama et al., 2004, "Retrospective statistical analysis of lyophilized protein formulations of progenipoietin using PLS: Determination of the critical parameters for long-term storage stability." Jour. Pharm. Sci. 93(10): 2609-2623.
Carpenter et al., 1997, "Rational design of stable lyophilized protein formulations: Some practical advice." Pharm. Research 14(8): 969-975.
Chang et al., 1996, "Physical factors affecting the storage stability of freeze-dried interleukin-1 receptor antagonist: Glass transition and protein conformation." Arch. Biochem. Biophys. 331(2): 249-258.
Webb et al., 2001, "A new mechanism for decreasing aggregation of recombinant human interferon-gama by a surfactant: Slowed dissolution of lyophilized formulations in a solution containing 0.03% polysorbate 20." Jour. Pharm. Sci. 91(2): 543-558.
Wang, 1999, "Instability, stabilization, and formulation of liquid protein pharmaceuticals." International Jour. Pharmceutics 185: 129-188.
Sharma and Kalonia, 2004, "Polyethylene glycol-induced precipitation of interferon alpha-2a followed by vacuum drying: development of a novel process for obtaining a dry, stable powder." AAPS PharmSci. 6(1):1-14.
Chang at al, 1996, "Development of a stable freeze-dried formulation of recombinant human interleukin-1 receptor antagonist." Pharm. Research 13(2): 243-249.

* cited by examiner

*Primary Examiner*—Bridget E Bunner
*Assistant Examiner*—Fozia M Hamud
(74) *Attorney, Agent, or Firm*—Valeta Gregg, Esq.; Tor Smeland, Esq.

(57) ABSTRACT

Formulations of an interleukin-1 (IL-1) antagonist are provided including a pre-lyophilized formulation, a reconstituted lyophilized formulation, and a stable liquid formulation. Preferably, the IL-1 antagonist is an IL-1 trap composed of a dimer of two fusion proteins having an amino acid sequence of SEQ ID NO: 10. Stable liquid formulations made with and without sodium chloride, and made with phosphate or histidine buffer, are provided.

12 Claims, 3 Drawing Sheets

STABLE LIQUID IL-1 ANTAGONIST FORMULATIONS

CROSS-REFERENCE TO RELATED APPLICATIONS

This application is a continuation-in-part application of U.S. Ser. No. 11/750,613, filed 18 May 2007, which is a continuation-in-part application of U.S. Ser. No. 11/205,935, filed 17 Aug. 2005, now U.S. Pat. No. 7,365,165, which claims the benefit under 35 USC § 119(e) of U.S. Provisional 60/602,137 filed 17 Aug. 2004, which applications are herein specifically incorporated by reference in their entirety.

BACKGROUND OF INVENTION

1. Field of the Invention

The present invention is directed to pharmaceutical formulations comprising agents capable of inhibiting interleukin-1 (IL-1), and to methods for making and using such formulations. The invention is directed to pharmaceutical formulations having increased stability.

2. Statement of Related Art

Interleukin-1 (IL-1) antagonists capable of blocking or inhibiting the biological action of IL-1, have been described. An example IL-1 antagonist, an IL-1 trap, is described in U.S. Pat. No. 6,927,044, herein specifically incorporated by reference in its entirety. The term "IL-1 trap" refers to an IL-1-binding fusion protein comprising a dimer of two fusion proteins, each having two IL-1 receptor components and a multimerizing component.

Lyophilization (freeze-drying under controlled conditions) is commonly used for long-term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of an interleukin-1 (IL-1) antagonist are provided. The stable formulations comprise an IL-1-binding protein with a pharmaceutically acceptable carrier. In specific embodiments, liquid and freeze-dried, or lyophilized formulations are provided.

In one aspect, a pre-lyophilization formulation of an interleukin-1 (IL-1) antagonist is provided, comprising an IL-1 protein antagonist capable of binding to and inhibiting the biological action of IL-1, a buffer, an organic co-solvent or bulking agent, and one or more lyoprotectants. In a specific embodiment, the IL-1 antagonist is a fusion protein capable of binding to IL-1, the buffer is histidine, the organic co-solvent or bulking agent is polyethylene glycol (PEG), and the lyoprotectant(s) is at least one of glycine, arginine, and sucrose. In one embodiment, the pre-lyophilized formulation does not contain a preservative.

In one embodiment of the pre-lyophilization formulation, the formulation comprises 5-100 mM histidine, 0.5-3.0% PEG, 0.25-3.0% glycine, 5-50 mM arginine, 0.5-30.0% sucrose, and 5-50 mg/ml of an IL-1 antagonist, at a pH of about 6.5. In one embodiment, the pre-lyophilization formulation may further comprise up to 5 mM citrate and/or 0.003-0.005% polysorbate. The polysorbate may be, for example, polysorbate 20 or 80.

In a more specific embodiment, a pre-lyophilization IL-1 antagonist formulation is provided that consists essentially of about 25 mg/ml IL-1 trap protein (SEQ ID NO: 10), 10-15 mM histidine, 0.8-1.0% PEG, 0.25-0.5% glycine, 15-20 mM arginine, and 0.5-1.0% sucrose. In a preferred embodiment, the formulation consists of 12.5 mM histidine, 0.94% PEG 3350, 0.31% glycine, 15.63 mM arginine, 0.63% sucrose, and 25 mg/ml of the IL-1 fusion protein having the sequence of SEQ ID NO:10, at a pH of about 6.5. In a specific embodiment, the pre-lyophilization formulation does not contain a preservative, a phosphate buffer, or more than trace amounts of NaCl. Citrate may be present in amounts of less than about 0.15 mM and up to about 0.005-0.01% polysorbate 20 may also be present.

In another aspect, a method of producing a lyophilized formulation of an IL-1 antagonist is provided, comprising subjecting a pre-lyophilization IL-1 antagonist formulation of the invention to lyophilization to generate a lyophilized IL-1 antagonist formulation. The lyophilized formulation may be lyophilized by any method known in the art for lyophilizing a liquid.

In a preferred embodiment, the lyophilization process comprises the steps of (i) cooling at 5° C.; (ii) freezing at −40° C.; (iii) annealing at −8° C.; (iv) freezing at −40° C.; (v) drying at 10° C.; (vi) drying at 40° C.; and (vii) cooling at 25° C. In a more specific embodiment, step (i) cooling is conducted for about 60 min; step (ii) freezing is conducted for about 120 min; step (iii) annealing is conducted for about 150 min; step (iv) freezing is conducted for about 120 min; step (v) drying is conducted for about 30 h; step (vi) drying is conducted for about 4 h; and/or step (vii) cooling is conducted for about 4 h.

In a more specific embodiment, a 25 mg/ml formulation of IL-1 trap protein is lyophilized as follows: vials containing the pre-lyophilized formulation are placed on a pre-cooled shelf at 5° C. and held at 5° C. for 60 min; temperature is ramped at 0.5° C./min to −40° C. and held at −40° C. for 120 min; temperature is ramped 0.5° C./min to −8° C. and held at −8° C. for 150 min; temperature is ramped at 0.5° C./min to −40° C. and held at −40° C. for 120 min; a vacuum is applied of 100 mTorr at a shelf temperature of −40° C.; temperature is ramped at 0.5° C./min to 10° C. and held at 10° C. for 30 h; temperature is ramped at 0.7° C./min to 40° C. and held at 40° C. for 4 h; temperature is ramped at 2° C./min to 25° C. and held at 25° C. for 4 h. The vials may be stoppered under a 608 Torr anhydrous nitrogen gas pressure to conclude lyophilization.

In another aspect, a lyophilized IL-1 antagonist formulation is provided that is made by lyophilizing an aqueous solution comprising 25 mg/ml IL-1 trap protein (SEQ ID NO:10), 10-15 mM histidine, 0.8-1.0% PEG, 0.25-0.5% glycine, 15-20 mM arginine, and 0.5-1.0% sucrose. In a preferred embodiment the lyophilized IL-1 trap formulation is lyophilized by (i) cooling at 5° C. for 60 min; (ii) freezing at −40° C. for 120 min; (iii) annealing at −8° C. for 150 min; (iv) freezing at −40° C. for 120 min; (v) drying at 10° C. for 30 h; (vi) drying at 40° C. for 4 h; and (vii) cooling at 25° C. for 4 h.

In another aspect, a lyophilized formulation of an IL-1 protein antagonist is provided that is capable of being reconstituted in an aqueous liquid in less than about three and a half minutes. In one embodiment, the lyophilized formulation is reconstituted in about one minute or less. In a specific embodiment, the aqueous liquid is water.

In another aspect, a lyophilized formulation of an IL-1 antagonist is provided that is capable of being reconstituted in a liquid with shaking, wherein following reconstitution at least 90% of the IL-1 antagonist is present in its native form as measured by size exclusion high performance liquid chromatography (SE-HPLC). In one embodiment, following reconstitution with shaking, at least about 95% of the IL-1 antagonist is present in its native form as measured by SE-HPLC. In another embodiment, at least about 98% of the IL-1 antagonist is present in its native form as measured by SE-HPLC.

In one embodiment, the lyophilized formulation is capable of being reconstituted at room temperature in water with vigorous shaking. In one embodiment, the shaking is carried out by vigorously agitating a mixture of the lyophilized formulation and water so that the mixture visibly bubbles and/or foams. In one embodiment, at least about 90% of the IL-1 antagonist of the reconstituted formulation is present in its native form as measured by SE-HPLC. In another embodiment, at least about 95% of the IL-1 antagonist of the reconstituted formulation is present in its native form as measured by SE-HPLC. In a more specific embodiment, at least about 95% of the IL-1 antagonist of the reconstituted formulation is present in its native form.

In another aspect, a lyophilized IL-1 antagonist formulation in a single dose unit is provided, wherein the IL-1 antagonist comprises the amino acid sequence of SEQ ID NO:10, and the lyophilized formulation is provided in a sterile container suitable for reconstitution as a liquid formulation for a single parenteral administration. In one embodiment, the container is a 20 ml glass vial. In another embodiment, the lyophilized formulation comprises about 220 mg of the IL-1 antagonist suitable for reconstitution as a liquid formulation having about 160 mg of withdrawable IL-1 antagonist. In another embodiment, the single dose is provided in a container suitable for reconstituting the lyophilized formulation to a volume of about 2.3 milliliters. In another embodiment, the single dose is provided in container that allows for a withdrawable content of about 2 milliliters. In another embodiment, the single dose comprises about 160 mg of the IL-1 antagonist. In another embodiment, the single dose unit is reconstitutable with water to a volume of about 2 milliliters and a concentration of about 80 mg/ml of IL-1 antagonist, about 40 mM histidine, about 50 mM arginine, about 3.0% polyethylene glycol 3350 (w/v), about 2% sucrose, and about 1% glycine (w/v), at a pH of 6.5±0.3. In another embodiment, the single dose does not include a preservative.

In another aspect, the invention features a method of producing a reconstituted lyophilized formulation of an IL-1 protein antagonist, comprising reconstituting the lyophilized formulation of the invention to a reconstituted formulation. In one embodiment, the IL:-1 protein antagonist of the reconstituted formulation is present at a concentration that is at least 3 times the concentration of the IL-1 protein antagonist of the pre-lyophilized formulation. In a preferred embodiment, a 25 mg/ml IL-1 trap protein formulation is lyophilized and reconstituted to an 80 mg/ml IL-1 trap protein formulation. In a specific embodiment, the lyophilized formulation is reconstituted with sterile water suitable for injection. In one embodiment, the reconstitution liquid may be bacteriostatic water. Reconstitution may include any suitable method, for example, by shaking or swirling.

In a another aspect, the invention features a stable liquid formulation of an IL-1 antagonist, comprising an IL-1 antagonist protein capable of binding to and inhibiting the biological action of IL-1, a buffer, an organic co-solvent, and one or more thermal stabilizers. In a specific embodiment, the IL-1 antagonist is an IL-1 trap fusion protein as shown in SEQ ID NO:10. In one embodiment, the buffer is a phosphate buffer. In another embodiment, the buffer is histidine. In one embodiment, the organic co-solvent agent is PEG, preferably PEG 3350. In one embodiment, the thermal stabilizers are NaCl and/or sucrose. More preferably, the thermal stabilizers are both NaCl and sucrose.

In a specific embodiment, the stable liquid formulation of an IL-1 antagonist comprises 5-100 mM phosphate buffer, 0.5-3% PEG, 25-150 mM NaCl, 5-30% sucrose, 10-500 mg/ml of an IL-1 trap protein, at a pH of about 6-6.5. In a more specific embodiment, the stable liquid formulation of an IL-1 antagonist comprises 10 mM phosphate buffer, 3% PEG 3350, 50 mM NaCl, 5-20% sucrose, 12.5-50 mg/ml of an IL-1 trap protein, at a pH of about 6-6.5. Additionally, low or trace amounts of a citrate buffer or polysorbate may be present. The stable liquid formulation of the IL-1 antagonist exhibits little or no precipitation as determined by visual inspection after storage of a 50 mg/ml IL-1 trap formulation for up to about 29 months at 5° C. Further, little or no aggregation is observed as determine by size-exclusion chromatography, e.g., HPLC, after storage of a 50 mg/ml IL-1 trap formulation for up to about 24 months at 5° C.

In another aspect, a stable liquid formulation is provided that comprises histidine, PEG, glycine, arginine, sucrose, and an IL-1 antagonist, wherein the formulation is pH 6-6.8.

In one embodiment, the stable liquid formulation comprises 40 mM histidine, 3% PEG, 1% glycine, 50 mM arginine, 2% sucrose, and 10 to 100 mg/ml IL-1 antagonist. In various embodiments the pH is 6.2-6.8. In a specific embodiment, the IL-1 antagonist is an IL-1 trap fusion protein comprising the amino acid sequence of SEQ ID NO:10 and is present at 80 mg/ml, and the PEG is PEG 3350. In a specific embodiment, the stable liquid formulation consists essentially of 40 mM histidine, 3% PEG 3350, 1% glycine, 50 mM arginine, 2% sucrose, and an IL-1 trap fusion protein at 80 mg/ml, wherein the IL-1 trap fusion protein comprises the amino acid sequence of SEQ ID NO:10 and the pH is 6.2 to 6.8. In specific embodiment, the pH is about 6.5.

In another aspect, a stable liquid formulation is provided that comprises sodium phosphate, PEG, glycine, arginine, sucrose, and an IL-1 antagonist, wherein the formulation is pH 6-6.8.

In one embodiment, the stable liquid formulation comprises 40 mM sodium phosphate, 3% PEG, 1% glycine, 50 mM arginine, 2% sucrose, and 10 to 100 mg/ml IL-1 antagonist. In a specific embodiment, the IL-1 antagonist is an IL-1 trap fusion protein comprising the amino acid sequence of SEQ ID NO:10 and is present at 80 mg/ml, the PEG is PEG 3350, and the pH is 6.2-6.8. In a specific embodiment, the stable liquid formulation consists essentially of 40 mM sodium phosphate, 3% PEG 3350, 1% glycine, 50 mM arginine, 2% sucrose, and an IL-1 trap fusion protein at 80 mg/ml, wherein the IL-1 trap fusion protein comprises the amino acid sequence of SEQ ID NO:10, and the pH is 6.2-6.8. In a specific embodiment, the pH is about 6.5.

In another aspect, a stable liquid formulation is provided that comprises phosphate, sodium chloride, PEG, sucrose, and an IL-1 antagonist, wherein the pH is 6-6.8.

In another embodiment, the stable liquid formulation comprises 10 mM phosphate, 50 mM NaCl, 3% PEG, 20% sucrose, and 10 to 100 mg/ml IL-1 antagonist, and the pH is 6.2-6.8. In a specific embodiment, the IL-1 antagonist is an IL-1 trap fusion protein comprising the amino acid sequence of SEQ ID NO:10, and is present at 10-50 mg/ml. In another embodiment, the IL-1 trap fusion protein is present at about 50 mg/ml. In a specific embodiment, the stable liquid formulation consists essentially of 10 mM sodium phosphate, 50 mM NaCl, 3% PEG 3350, 20% sucrose, and an IL-1 trap fusion protein at 50 mg/ml, wherein the IL-1 trap fusion protein comprises the amino acid sequence of SEQ ID NO:10, and the pH is 6.2-6.8. In a specific embodiment, the pH is about 6.5.

In various embodiments of the stable liquid formulation, small amounts of other substances that do no substantially reduce the stability of the formulation can be present. For example, the stable liquid formulation can include small amounts of polysorbate(s) and/or citrate.

In another aspect, a receptacle containing a stable liquid formulation of an IL-1 antagonist is provided. The stable liquid formulation is selected from the stable liquid formulations described herein. In various embodiments, the receptacle contains an amount of the stable liquid formulation extractable as a single dose. In a specific embodiment, the amount of the single injectable dose is one ml to two ml.

In another aspect, a pre-filled syringe is provided containing a stable liquid formulation of an IL-1 antagonist selected from the stable liquid formulations described herein. In various embodiments, the pre-filled syringe comprises a single injectable dose of the stable liquid formulation. In a specific embodiment, the pre-filled syringe comprises a sterile single injectable dose of the stable liquid formulation.

In another aspect, a pre-filled dual-chambered syringe comprising a first chamber and a second chamber is provided, comprising in the first chamber a lyophilized formulation of an IL-1 antagonist and comprising in the second chamber a liquid that is suitable for reconstituting the lyophilized formulation of the IL-1 antagonist. In one embodiment, lyophilization of the IL-1 antagonist is carried out in the first chamber. In various embodiments, the first chamber comprises a lyophilized formulation as described herein, and the second chamber comprises a liquid as described herein that is suitable for reconstituting the lyophilized formulation of the first chamber. In a specific embodiment, the dual-chambered syringe comprises a single injectable dose of an IL-1 trap as described herein. In another embodiment, the dual-chambered syringe is a single-use dual chambered syringe. In a specific embodiment, the dual-chambered syringe is a VETTER LYO-JECT™ device.

In another aspect, a pre-filled dual-chambered receptacle comprising a first chamber and a second chamber is provided, comprising in the first chamber a lyophilized formulation of an IL-1 antagonist, and comprising in the second chamber a liquid that is suitable for reconstituting the lyophilized formulation of the IL-1 antagonist. In various embodiments, the first chamber comprises a lyophilized formulation as described herein, and the second chamber comprises a liquid as described herein that is suitable for reconstituting the lyophilized formulation of the first chamber. In a specific embodiment, the dual-chambered receptacle comprises a single injectable dose of an IL-1 trap as described herein. In another embodiment, the dual-chambered receptacle is a single-use dual chambered receptacle. In a specific embodiment, the dual-chambered receptacle is a VETTER V-LK™ dual chamber cartridge.

Unless otherwise specified or apparent from the context, any feature of the invention can be used in conjunction with any other feature of the invention. Other objects and advantages will become apparent from a review of the ensuing detailed description.

DETAILED DESCRIPTION OF THE INVENTION

Figure 1:
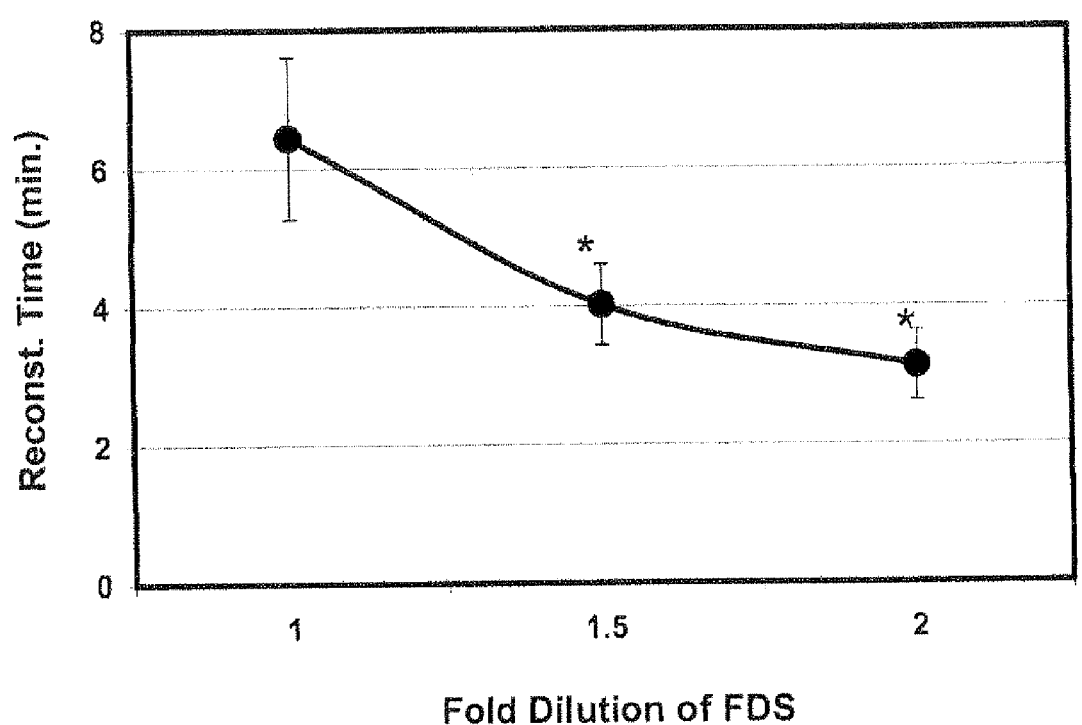
FIG. 1. Effect of dilution of pre-lyophilized IL-1 trap protein formulation on reconstitution time. IL-1 trap protein (SEQ ID NO:10) formulations were 40 mg/ml IL-1 trap protein, 20 mM histidine, 1.5% PEG 3350, 1% sucrose, 0.5% glycine, 25 mM arginine, pH 6.5 (control); 25 mg/ml IL-1 trap protein, 12.5 mM histidine, 0.94% PEG 3350, 0.63% sucrose, 0.31% glycine, 15.6 mM arginine, pH 6.5; and 20 mg/ml IL-1 trap protein, 10 mM histidine, 0.75% PEG 3350, 0.5% sucrose, 0.25% glycine, 12.5 mM arginine, pH 6.5. n=5, *p<0.05 vs. control, Student's t-test.

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

As used in this specification and the appended claims the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation and other degenerative processes while in the freeze-dried state. The lyophilized protein is normally reconstituted with water optionally containing a bacteriostatic preservative (e.g., benzyl alcohol) prior to administration.

Definitions

By the term "therapeutically or pharmaceutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker", "inhibitor", or "antagonist" is meant a substance that retards or prevents a chemical or physiological reaction or response. Common blockers or inhibitors include, but are not limited to, antisense molecules, antibodies, antagonists and their derivatives.

The term "pharmaceutically acceptable" includes approval by a regulatory agency of the federal or a state government or listed in the U.S. Pharmacopeia or other generally recognized pharmacopeia for use in animals, and more particularly in humans.

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine) acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g, zinc sulfate), thimerosal, methylparaben, propylparaben, carboxymethylcellulose, chlorobutanol, and heparin.

The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Generally, acceptable bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers. In the formulations of the invention, PEG 3350 is an organic co-solvent which is used to stabilize the IL-1 protein antagonist when agitated, mixed or handled, and as a bulking agent to help produce an acceptable bulk.

The term "lyoprotectant" includes a substance that may be added to a freeze-dried or lyophilized formulation to help maintain protein structure when freeze-dried or lyophilized.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP.

IL-1 Antagonists

An IL-1 antagonist is a compound capable of blocking or inhibiting the biological action of IL-1, including fusion proteins capable of trapping IL-1, such as an IL-1 trap. In a preferred embodiment, the IL-1 trap is a dimer of two IL-1-specific fusion proteins, each comprising two IL-1 receptor components and a multimerizing component, for example, an IL-1 trap described in U.S. Pat. No. 6,927,044, issued Aug. 9, 2005, herein specifically incorporated by reference in its entirety. In a specific embodiment, the IL-1 trap is the fusion protein shown in SEQ ID NO:2, 4, 6, 8, 10, 12, 14, 16, 18, 20, 22, 24, 26. A preferred IL-1 trap is shown in SEQ ID NO:10. The invention encompasses the use of an IL-1 trap substantially identical to the protein of SEQ ID NO: 2, 4, 6, 8, 10, 12, 14, 16, 18, 20, 22, 24, 26, that is, a protein having at least 95% identity, preferably at least 97% identity, and more preferably at least 98% identity to the protein of SEQ ID NO: 2, 4, 6, 8, 10, 12, 14, 16, 18, 20, 22, 24, 26 and capable of binding and inhibiting IL-1. Further, in specific embodiments, the IL-1 antagonist is a modified IL-1 trap comprising one or more receptor components and one or more immunoglobulin-derived components specific for IL-1 and/or an IL-1 receptor. In another embodiment, the IL-1 antagonist is a modified IL-1 trap comprising one or more immunoglobulin-derived components specific for IL-1 and/or an IL-1 receptor.

In another embodiment, the IL-1 antagonist is an IL-1 trap that is a dimeric fusion protein having extracellular domains of human cytokine receptor IL-1 and the Fc portion of human IgG1 in a single dimeric molecule, wherein the extracellular domains are the IL-1 Type I receptor (IL-1RI) and the IL-1 receptor accessory protein (AcP), wherein the dimer is covalently linked by disulfide bonds in the Fc region, and wherein the dimer has a molecular weight of about 252 kDa of which about 80% is protein (about 201 kDa) and about 20% is carbohydrate.

The IL-1 trap of the methods and formulations of the invention can be prepared by any suitable method known in the art, or that comes to be known, that is useful in preparing an IL-1 trap. The IL-1 trap is preferably substantially free of protein contaminants at the time it is used to prepare the pharmaceutically acceptable formulation. By "substantially free of protein contaminants" is meant, preferably, that at least 90% of the weight of protein of an IL-1 trap preparation used for making a formulation comprising an IL-1 trap is IL-1 trap protein, more preferably at least 95%, most preferably at least 99%. The IL-1 trap is preferably substantially free of aggregates. "Substantially free of aggregates" means that at least 90% of the weight of IL-1 trap protein is not present in an aggregate at the time the IL-1 trap is used to prepare the pharmaceutically effective formulation.

The IL-1 trap of the methods and formulations of the invention may contain low or trace amounts of compounds as a results of the purification process, for example, low or trace amounts of citrate and/or polysorbate. In one embodiment of the pre-lyophilization formulation of the invention containing about 40 mg of IL-1 trap/ml, citrate may be present at a concentration of about 0.1 mM and/or polysorbate may be present at a concentration of about 0.004%. If the pre-lyophilization formulation is reconstituted after lyophilization to half of the original volume (e.g., 80 mg/ml of IL-1 trap), the resulting concentrations may be 0.2 mM citrate and/or 0.008% polysorbate. If the pre-lyophilization formulation is reconstituted after lyophilization to a third of the original volume (e.g., 120 mg/ml of IL-1 trap), the resulting concentrations may be 0.6 mM citrate and/or 0.012% polysorbate, Lyophilization and Lyophilized Formulations In one aspect of the invention, a pharmaceutically acceptable formulation comprising an IL-1 trap is provided, wherein the formulation is a freeze-dried or lyophilized formulation. Preferably, the freeze-dried or lyophilized formulation comprises a pharmaceutically effective amount of an IL-1 trap. Lyophilized formulations can be reconstituted into solutions, suspensions, emulsions, or any other suitable form for administration or use. Lyophilized formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.). Preferably, lyophilized formulations are stored below about 25° C., more preferably, at about 4-20° C.; below about 4° C.; below about −20° C.; about −40° C.; or about −70° C.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution. A preferred liquid formulation used to generate a freeze-dried or lyophilized formulation comprises an IL-1 trap in a pharmaceutically effective amount, a buffer, a stabilizer, and a bulking agent. Freeze-dried or lyophilized formulations preferably comprise histidine, since histidine, in comparison to phosphate, is more effective at stabilizing the IL-1 trap when the IL-1 trap is lyophilized. Organic co-solvents, such as PEG 3350, are used to stabilize the IL-1 trap when agitated, mixed, or handled. A lyoprotectant is preferably used in freeze-dried or lyophilized formulations. Lyoprotectants help to maintain the secondary structure of proteins when freeze-dried or lyophilized. Three preferred example lyoprotectants are glycine, arginine, and sucrose, which are preferably used together.

Stable Liquid Formulations

Stable liquid formulations of IL-1 antagonists are provided. The stable liquid formulations include pharmaceutically acceptable formulations comprising an IL-1 antagonist that is an IL-1 trap as described herein, e.g., an IL-1 trap comprising the sequence of SEQ ID NO:10. The formulations may be stored for extended periods (e.g., from several days to months, to a year or more, and in various embodiments up to about two years) at a temperature of around 2° C. to 8° C. (e.g., about 5° C.). In various embodiments, the stable liquid formulations can be reconstituted from lyophilized formulations, or can be prepared without a lyophilization/reconstitution step.

Stable liquid formulations can be made with or without sodium chloride. Stable liquid formulations made without sodium chloride include formulations comprising histidine, PEG, glycine, arginine, sucrose, and an IL-1 antagonist, at pH 6.2-6.8. Stable liquid formulations made with added sodium chloride include formulations comprising phosphate, sodium chloride, PEG, sucrose and an IL-1 antagonist, at pH 6.2-6.8. Such stable liquid formulations exhibit a good stability when stored lower than room temperature, e.g., at about 2-8° C., or about 5° C., for days, weeks, months, and even for at least about two years in various embodiments, where stability is measured by recovery of IL-1 trap and native IL-1 trap (by, e.g., SE-HPLC) from the stored formulations.

Stable liquid formulations include those suitable for administration to humans. Accordingly, stable liquid formulations can comprise a pharmaceutically effective amount of an IL-1 trap at a concentration suitable for parenteral administration. A pharmaceutically effective amount of an IL-1 trap as described herein includes, for example, 10-100 mg of a dimeric IL-1 trap fusion protein, delivered, for example, in a stable liquid formulation of about 1 to about 2 ml. In a specific embodiment, a pharmaceutically effective amount of IL-1 trap is delivered in about 2 ml of a stable liquid formulation having about 10 to about 50 mg/ml, 12.5 mg/ml, about 25 mg/ml, about 50 mg/ml, or about 80 mg/ml of dimeric IL-1 trap fusion protein.

The stable liquid formulations, for example those suitable for parenteral administration, can be stored in a receptacle or container, including in a container or receptacle containing an amount of a stable liquid formulation extractable as a single dose, for example, a container or receptacle having about one to about two milliliters of a stable liquid formulation described herein.

One suitable container for the stable liquid formulations is a syringe containing a pharmaceutically effective amount of an IL-1 trap in a stable formulation as described herein. The syringe can be pre-filled with a single injectable dose of the stable liquid formulation.

EXAMPLES

Example 1

Stability of Pre-lyophilized and Lyophilized Formulations

The stability of pre-lyophilized and lyophilized formulations was determined. A pre-lyophilized formulation containing 40 mg/ml IL-1 trap (SEQ ID NO:10), 20 mM histidine, 1.5% PEG-3350, 1% sucrose, 0.5% glycine, 25 mM arginine-HCl, pH 6.5 was incubated at 5° C. for 0-52 weeks. As shown in Table 1, the native (non-aggregated) form of IL-1 decreased from 94.9 (0 weeks) to 92.3 (52 weeks), and the percent aggregate increased from 1% to 1.8% in the same time period.

TABLE 1

Stability of a Pre-Lyophilized Formulation

| Incubation time (weeks at 5° C.) | % Native | % Aggregate |
|---|---|---|
| 0 | 94.9 | 1.0 |
| 4 | 94.3 | 1.3 |
| 12 | 93.5 | 1.7 |
| 24 | 93.3 | 1.5 |
| 36 | 92.6 | 1.5 |
| 52 | 92.3 | 1.8 |

The stability of a lyophilized formulation containing 40 mg/ml IL-1 trap (SEQ ID NO:10), 20 mM histidine, 1.5% PEG-3350, 1% sucrose, 0.5% glycine, 25 mM arginine-HCl, pH 6.5 (pre-lyophilized concentrations) was incubated at 25° C. for 0-56 weeks. As shown in Table 2, the native (non-aggregated) form of IL-1 decreased from 97.0 (0 weeks) to 94.0 (56 weeks), and the percent aggregate increased from 0.8% to 3.6% in the same time period.

TABLE 2

Stability of a Lyophilized Formulation

| Incubation time (weeks at 25° C.) | % Native | % Aggregate |
|---|---|---|
| 0 | 97.0 | 0.8 |
| 3.9 | 96.3 | 1.4 |
| 6.1 | 95.5 | 1.5 |
| 12.3 | 95.4 | 1.9 |
| 25.7 | 94.7 | 2.2 |
| 39.3 | 94.4 | 2.9 |
| 56 | 94.0 | 3.6 |

Example 2

Effect of Drug Substance Concentration and Fill Volume on Reconstitution Time Experiments were undertaken to determine the effect of concentration of pre-lyophilized formulations of IL-1 antagonist on time required to reconstitute the final solution. A pre-lyophilized formula containing 40 mg/ml IL-1 trap protein (SEQ ID NO:10) in 20 mM histidine at pH 6.5, 1.5% PEG 3350, 1% sucrose, 0.5% glycine, 25 mM arginine-HCl (control) or diluted formulations were tested. A 1.6-fold dilution of the pre-lyophilization preparation from 40 mg/ml IL-1 trap protein to 25 mg/ml IL-1 trap protein was found to reduce reconstitution time by 36% without necessitating a lengthy freeze-drying process during lyophilization (FIG. 1).

Example 3

Effect of Lyophilization Methods on Reconstitution Time

The process of lyophilization was modified to include an annealing step to reduce the length of primary drying and eliminated crack development in the lyophilized cake. Optimization of the lyophilization process to reduce the length of the drying process included increasing the shelf temperature during primary and secondary drying steps. Product stability, final moisture content, and cake appearance were used to evaluate the feasibility of the different process conditions.

Freezing/Annealing. The process of annealing involves holding the frozen product above the glass transition temperature (Tg') of the formulation prior to the initiation of vacuum. Such a step may allow for crystal growth of excipients that did not fully crystallize during the initial freezing step, as well as reducing freezing-induced heterogeneity in drying rate through Ostwald ripening. Annealing has been reported to affect reconstitution times, secondary structure in the dried state, cracking in dried cakes, and aggregation of reconstituted product (see, for example, Webb et. al. (2003) J Pharmaceutical Sci 92:715-729).

Figure 2:
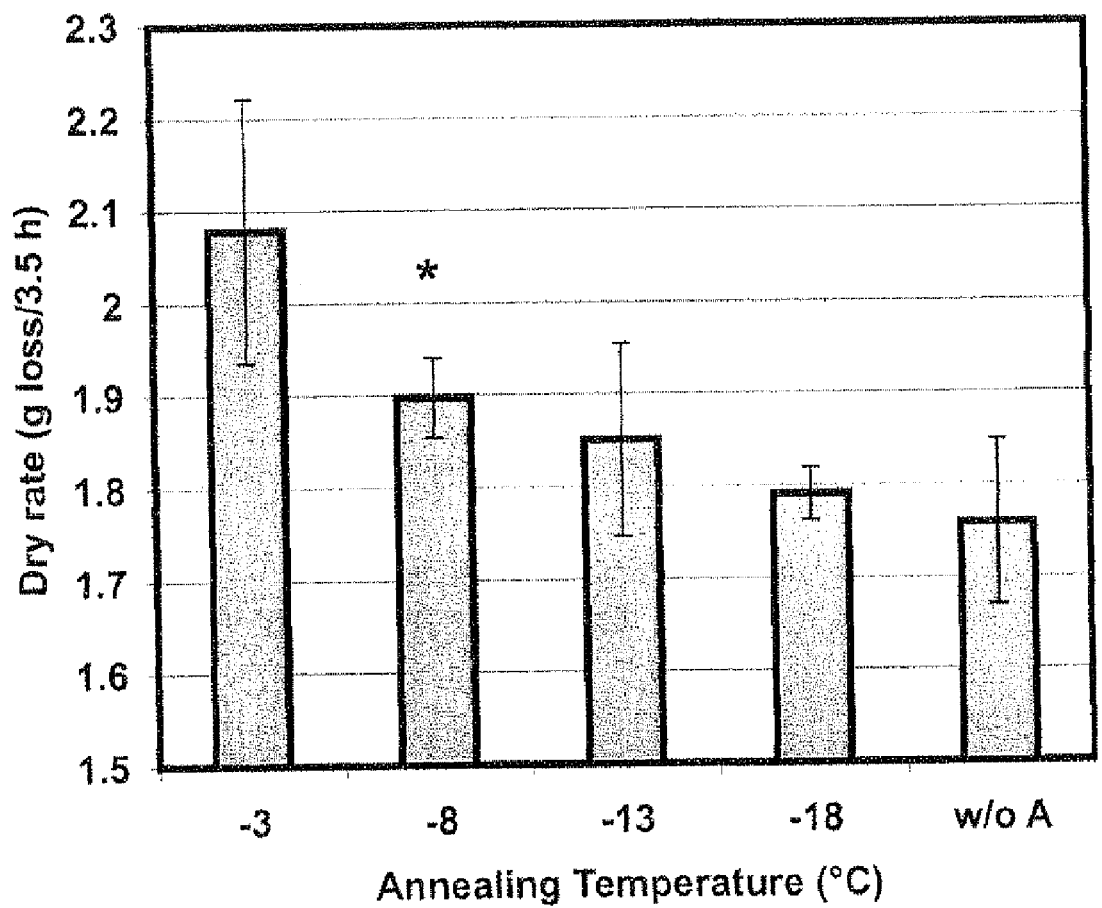
FIG. 2. Effect of annealing temperature on primary drying time of a 25 mg/ml IL-1 trap protein formulation (described above), n=5. Annealing hold time=3 hrs. Control=without annealing step. *One-way ANOVA test compared to control.

Annealing Temperature Optimization. Twenty ml vials were filled with 8.8 ml of 25 mg/ml IL-1 trap protein pre-lyophilization formulation and weighed. Sample vials were put in the freeze-dryer with a shelf temperature of 5° C. for 1 hour, frozen at −40° C. for 2 hours, annealed for 3 hours at either −3° C., −8° C., −13° C., or −18° C., and re-solidified at −40° C. for 1 hour. The shelf temperature ramp rate was 0.5° C./min in all of the above steps. The control unannealed sample vials were cooled and frozen as described above. All vials underwent primary drying in the same cycle. At the completion of the annealing step, all control and annealing test vials were transferred to the −40° C. shelf in the freeze-dryer for 1 hour as described above. Sublimation was initiated by first reducing the chamber pressure to 100 mTorr and then raising the shelf temperature to −5° C. Vials were stoppered after 5.5 h, during which 20-50% of the crystalline water has sublimed. The vials were re-weighed on removal from the freeze-dryer, and the primary drying rate was calculated using the weight lost during the partial drying. Compared to control vials without annealing or annealing at −13° C. or −18° C., cycles incorporating annealing steps at −3° C. or −8° C. had a significantly higher rate of sublimation (FIG. 2).

Figure 3:
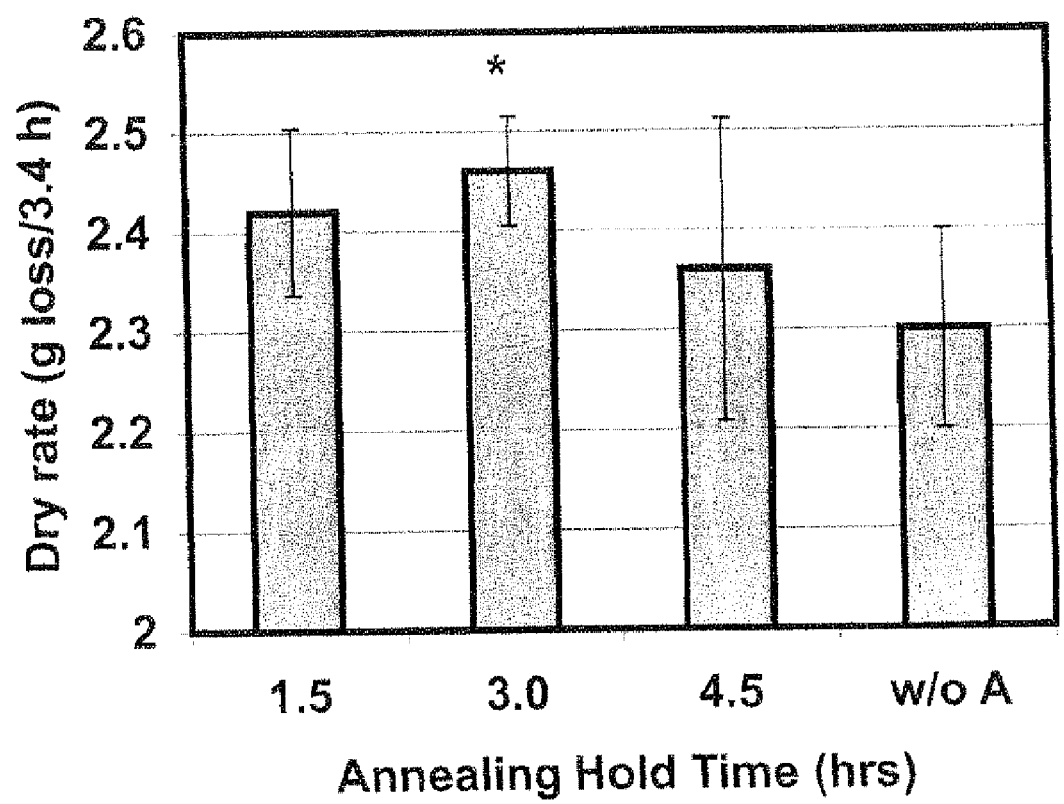
FIG. 3. Effect of annealing time on rate of primary drying. N=5. *p<0.05 one-way ANOVA test compared to control.

Annealing Time Optimization. Twenty ml vials were filled with 8.8 ml of 25 mg/ml IL-1 trap protein pre-lyophilization formulation and weighed. Sample vials were put in the freeze-dryer with a shelf temperature of 5° C. for 1 hour, frozen at −40° C. for 2 hr, annealed at −6° C. for either 1.5 hours, 3 hours, or 4 hours, and re-solidified at −40° C. for 1 h. The shelf temperature ramp rate was 0.5° C./min in all of the above steps. The control unannealed samples vials were cooled and frozen as described above. Sublimation was initiated by first reducing the chamber pressure to 100 mTorr and then raising the shelf temperature to −5° C. Vials were stoppered after 5.5 h. The vials were re-weighed on removal from the freeze-dryer, and the primary drying rate was calculated using the weight lost during the partial drying. Compared to the control that had no annealing step, only the 3 hour annealing step had a significant lowering of the sublimation rate (FIG. 3). An annealing time of 2.5 hours was chosen. The incorporation of this annealing step (−8° C. hold for 2.5 hours) in the lyophilization cycle resulted in vials that can be reconstituted in ~60% of the time required to reconstitute the vials lyophilized without the annealing step. Combining the dilution of the pre-lyophilization formula and the incorporation of the annealing step shortened the reconstitution time of the resulting cake regardless of the method employed for reconstitution, as well as eliminating deep cracks in the resulting freeze-dried cakes.

Primary Drying. To determine the target product temperature for primary drying, the glass transition temperature (Tg') was determined to be −20° C. by subambient modulated differential scanning calorimetry (mDSC). The collapse temperature (Tc) is determined by freeze-drying microscopy. A maximum allowable product temperature of −23° C. was selected to provide a 3° C. safety margin during primary drying.

Secondary Drying. The chamber pressure was fixed at 100 mTorr for development of this lyophilization cycle. Although the length of secondary drying time is important for lowering moisture, the shelf temperature may be more important (see, for example, Pikal, "Freeze-Drying of Proteins Part 1: Process Design", Biopharm, September 1990.). A 25° C. shelf temperature was examined as a conservative but likely viable secondary drying step, while the secondary drying step of 40° C. was examined as a faster cycle due to decreased overall drying time. Secondary drying at both shelf temperatures met the target moisture content of less than 1% by Karl Fischer titration. In addition, the stability of the products generated from the 2 different secondary drying shelf temperatures was not significantly different. A similar amount of degradation was observed when lyophilized Drug Product produced from both secondary drying temperatures was stored at 50° C. or 40° C. for 4 weeks. No impact on the reconstitution time, pH, moisture content, or quality of the cake was observed. Therefore, a shelf temperature for secondary drying of 40° C. was chosen to shorten the length of secondary drying and the overall length of the cycle. Accordingly, the optimized lyophilization cycle, having a total time of approximately 52 hours, contained the following steps:

(1) Cool: vials containing the pre-lyophilization formulation are placed on pre-cooled shelf at 5° C. and held at 5° C. for 60 min; (2) Freeze: temperature is reduced 0.5° C./min to −40° C. and held at −40° C. for 120 min; (3) Anneal: temperature is increased 0.5° C./min to −8° C. and held at −8° C. for 150 min; (4) Freeze: temperature is reduced 0.5° C./min to −40° C. and held at −40° C. for 120 min; (5) drying by applying a vacuum of 100 mTorr at a shelf temperature of −40° C.; (6) Primary drying: temperature changed 0.5° C./min to 10° C. and held at 10° C. for 30 h; (7) Secondary drying: temperature changed 0.7° C./min to 40° C. and held at 40° C. for 4 h; (8) Cooling secondary drying: temperature changed 2° C./min to 25° C. and held at 25° C. for 4 h.

The physical attributes of the lyophilized product examined were cake appearance, moisture, crystallinity, melting temperature (Tm), reconstitution time and turbidity of reconstituted solution. In addition, maintenance of secondary structure in the dried state compared to liquid was monitored by FTIR analysis. Cake appearance was recorded via a digital photograph of representative vials. No cracks were visible, no collapse of the cake occurred, and no meltback was observed. The moisture content was less than 0.1%. Polarized light microscopy was employed to assess the physical form of the drug product. The freeze-dried product showed no birefringence, indicating the absence of crystallinity. The control, LiCl powder showed birefringence as a typical crystalline solid. Analysis by modulated differential scanning calorimetry (mDSC), showed a thermal transition at approximately 56° C. The same signal has also been reported from other PEG-containing products and is believed to correspond to the phase transition of PEG. After reconstitution with 2.3 ml sterile water for injection, no significant increase in turbidity was measured at 405 nm, indicating no significant particulates were produced during the lyophilization and reconstitution processes. IL-1 trap protein remained stable during lyophilization and reconstitution. Purity, as determined by SE-HPLC (size exclusion high performance liquid chromatography) and non-reducing SDS-PAGE indicated only a slight increase in aggregate, that may be within the experimental error of the gel scanning equipment, compared to pre-lyophilization liquid. FTIR spectra in the amide I region of the pre-lyophilized and reconstituted product were superimposable, indicating the secondary structure was maintained through the lyophilization and the reconstitution processes.

Effect of Shaking on Reconstitution Time. Following addition of liquid, reconstitution by shaking resulted in the rapid reconstitution of the lyophilized product to the 80 mg/ml IL-1 trap protein formulation (Table 3). Reconstitution was performed by shaking the vial until the cake was completely reconstituted. Compared to the lyophilized 40 mg/ml IL-1 trap protein formulation, reconstitution of the lyophilized 25 mg/ml IL-1 trap protein formulation not only reduced the average reconstitution time but reduced the variability in the reconstitution times. The reduced variability is observed in a lower standard deviation and in a reduction in the difference observed between the maximum and minimum reconstitution times.

TABLE 3

Reconstitution Time as a Function of Concentration of Pre-Lyophilization Formula IL-1 Trap Formulation

| FORMULATION/DOSE FORM | 40 mg/ml FORMULATION (n = 20) | 25 mg/ml FORMULATION (n = 20) |
| --- | --- | --- |
| Reconstitution Time | 97 ± 50 sec | 23 ± 6 sec |
| Maximum Time | 3 min 20 sec | 36 sec |
| Minimum Time | 49 sec | 11 sec |

Reconstituted products were analyzed by SE-HPLC and FTIR (Tables 4 and 5). Reconstitution by the shaking method had no detrimental effect on either the recovery of the protein or the purity as determined by SE-HPLC. The stability of reconstituted product also examined when reconstituted by vigorous shaking. This process involved shaking the vials as hard as possible, holding the top and bottom of the vial between two fingers. Despite the vigorous shaking, no significant increase in molecular weight variants was observed as determined by SE-HPLC analysis. No differences are observed in the stability of the product when reconstituted by either the swirling or shaking methods. In addition, FTIR analysis showed no differences in the secondary structure of IL-1 trap protein due to a reconstitution method (*Recovery determined by SE-HPLC).

TABLE 4

Reconstitution of Lyophilized 40 mg/ml IL-1 Trap Protein

| | RECONSTITUTION METHOD | | | | | |
| --- | --- | --- | --- | --- | --- | --- |
| | SWIRLING | | SHAKING | | VIGOROUS SHAKING | |
| | Protein Recovered (mg/ml)* | % Native Remaining (SE-HPLC) | Protein Recovered (mg/ml)* | % Native Remaining (SE-HPLC) | Protein Recovered (mg/ml)* | % Native Remaining (SE-HPLC) |
| Pre-Lyo | 38 | 96.7 | 38 | 96.7 | 37 | 96.8 |
| Post-Lyo | 79 | 96.2 | 86 | 96.4 | 79 | 96.6 |

TABLE 5

Reconstitution of Lyophilized 25 mg/ml IL-1 Trap Protein

| | RECONSTITUTION METHOD | | | |
|---|---|---|---|---|
| | SWIRLING | | SHAKING | |
| | Protein Recovered (mg/ml)* | % Native Remaining (SE-HPLC) | Protein Recovered (mg/ml)* | % Native Remaining (SE-HPLC) |
| Pre-Lyo | 24 | 96.7 | 24 | 96.7 |
| Post-Lyo | 78 | 96.8 | 80 | 96.1 |

Reconstitution of lyophilized IL-1 trap using either the shaking or swirling methods had no adverse effect on the integrity of the protein, as determined by quantitative scan and visual inspection of Coomassie-stained non-reducing SDS-PAGE gels, and by measurement of IL-1 trap potency in a bioassay and in a binding assay. Oligosaccharide profiling assays showed no difference in sialic acid composition of the IL-1 trap between reconstitution by swirling and reconstitution by shaking. FTIR analysis of a pre-lyophilized preparation and reconstituted samples prepared by the swirling method and the shaking method showed no significant differences in the FTIR spectrum (about 1700 to about 1600 cm$^{-1}$), including in the amide I region.

Example 4

Stable Liquid Formulations

In one aspect, the invention provides a stable pharmaceutically acceptable formulation comprising an IL-1 trap, wherein the formulation is a liquid formulation. Preferably, the liquid formulation comprises a pharmaceutically effective amount of an IL-1 trap. The formulation can also comprise one or more pharmaceutically acceptable carriers, buffers, bulking agents, stabilizers, preservatives, and/or excipients. An example of a pharmaceutically acceptable liquid formulation comprising an IL-1 trap comprises an IL-1 trap in a pharmaceutically effective amount, a buffer, a co-solvent, and one or more stabilizers.

A preferred liquid formulation comprises phosphate buffer, an organic co-solvent, and one or more thermal stabilizers to minimize formation of aggregates and low molecular weight products when stored, and about 12.5 mg/ml to about 50 mg/ml IL-1 trap, wherein the formulation is from about pH 6.0 to about pH 6.75. A more preferred liquid formulation comprises 10 mM phosphate buffer, 3% PEG, 50 mM NaCl, 5-20% sucrose, and 10-100 mg/ml IL-1 trap, wherein the formulation is at a pH of about 6.0 to about 6.5. Although either NaCl or sucrose can be used as a stabilizer, a combination of NaCl and sucrose has been established to stabilize the IL-1 trap more effectively than either individual stabilizer alone. Preferably, PEG is PEG 3350, which has been established to enhance IL-1 trap stability.

Table 6 shows the percent of native IL-1 trap or percent aggregated IL-1 trap in samples containing either 5 or 20% sucrose as determined over a period of up to 24 months when incubated at 5° C. In the presence of 20% sucrose, the native (non-aggregated) form of IL-1 trap dropped from 92.6% at day 0 to 88.9% at 24 months and the percentage aggregate increased from 2.3% to 3.4% over the same time period. The 5% sucrose formulation had a native (non-aggregated) form of IL-1 trap dropped from 92.4% at day 0 to 86.9% at 24 months and the percentage aggregate increased from 2.6% to 3.6% over the same time period

TABLE 6

Native and Aggregate IL-1 Trap as a Function of Time and Sucrose at 5° C.

| | 20% Sucrose | | 5% Sucrose | |
|---|---|---|---|---|
| Incubation time at 5° C. (months) | Native (%) | Aggregate (%) | Native (%) | Aggregate (%) |
| 0 | 92.6 | 2.3 | 92.4 | 2.6 |
| 1.0 | 92.6 | 2.4 | 92.5 | 2.5 |
| 2.0 | 91.9 | 2.6 | 91.5 | 2.9 |
| 6.0 | 91.6 | 2.8 | 91.0 | 2.9 |
| 18 | 91.8 | 3.2 | 90.7 | 3.6 |
| 21.0 | 91.3 | 2.9 | 89.5 | 3.6 |
| 24.0 | 88.9 | 3.4 | 86.9 | 3.6 |

Table 7 shows the percent of native IL-1 trap in samples containing either 0, 5 or 20% sucrose as determined over a period of up to 2.9 months when incubated at 5° C. (50 mg/ml IL-1 trap, 10 mM Phosphate, 0.2% polysorbate-20, 50 or 135 (with 0% sucrose) mM NaCl, pH 6.5. In the presence of 0% sucrose, the native (non-aggregated) form of IL-1 trap dropped from 96.4% at day 0 to 0.5% at 2.9 months. The 5% sucrose formulation had a native (non-aggregated) form of IL-1 trap which dropped from 96.5% at day 0 to 39.2% at 2.9 months. The 20% sucrose formulation had a native (non-aggregated) form of IL-1 trap which dropped from 96.4% at day 0 to 95.3% at 2.9 months.

TABLE 7

% Native IL-1 Trap as a Function of Time and Sucrose Concentration at 5° C.

| Incubation Time | PERCENT NATIVE | | |
|---|---|---|---|
| (months) | 0% Sucrose | 5% Sucrose | 20% Sucrose |
| 0 | 96.4 | 96.5 | 96.4 |
| 1 | 96.7 | 89.3 | 96.2 |
| 2.9 | 0.5 | 39.2 | 95.3 |

Table 8 shows the stability over an extended period of time of a stable liquid formulation of an IL-1 trap protein (a dimeric fusion protein containing the amino acid sequence of SEQ ID NO:10) at 50 mg/ml in 10 mM sodium phosphate, 50 mM NaCl, 20% sucrose, 3% PEG 3350, pH 6.5. Briefly, the stable liquid formulation was prepared and stored for 730 days at about 5° C. (2° C. to 8° C.). The percent of IL-1 trap recovered and native IL-1 trap recovered was measured by SE-HPLC, and was determined at 29, 60, 547, 630, and 730 days. As Table 8 illustrates, the IL-1 trap in the liquid formulation was stable throughout the period.

TABLE 8

Native IL-1 Trap as a Function of Time at 5° C.

| Length of Stress (days) | Recovered (%) | Native (%) |
|---|---|---|
| 0 | 100 | 92.6 |
| 29 | 101 | 92.5 |
| 60 | 110 | 91.8 |
| 180 | 99 | 91.6 |
| 547 | 102 | 91.3 |
| 630 | 92 | 91.3 |
| 730 | 96 | 88.9 |

Example 5

Stable Liquid Formulations without NaCl

Liquid formulations of IL-1 trap fusion protein were prepared without added NaCl and displayed good stability over an extended period of time. Table 9 shows the stability over an extended period of time of a liquid formulation of an IL-1 trap protein (a dimeric fusion protein containing the amino acid sequence of SEQ ID NO:10) at 80 mg/ml in 40 mM histidine, 3% PEG 3350, 1% glycine, 50 mM arginine, and 2\ % sucrose, pH about 6.5. Briefly, the stable liquid formulation was prepared and stored for up to 676 days at about 5° C. (2° C. to 8° C.). The percent of IL-1 trap recovered and native IL-1 trap recovered was measured by SE-HPLC, and determined at 4, 29, 88, 209, 385, and 676 days. The pH of the formulation was about 6.3, and none of the formulations exhibited any significant turbidity as measured by optical density at 405 nm ($OD_{405} \leq 0.01$). Values in Table 9 are averages of 3 individual samples. As Table 9 illustrates, the IL-1 trap in the liquid formulation was stable throughout the period.

TABLE 9

Native IL-1 Trap in the Absence of NaCl as a Function of Time at 5° C.

| Length of Stress (days) | Recovered (mg/ml) | Native (%) |
|---|---|---|
| 0 | 77 | 95.7 |
| 4 | 74 | 95.6 |
| 29 | 77 | 95.5 |
| 88 | 79 | 95.0 |
| 209 | 76 | 94.7 |
| 385 | 76 | 94.4 |
| 676 | 78 | 93.3 |

Formulations, whether liquid or freeze-dried and lyophilized, can be stored in an oxygen-deprived environment. Oxygen-deprived environments can be generated by storing the formulations under an inert gas such as, for example, argon, nitrogen, or helium.

Although the foregoing invention has been described in some detail by way of illustration and examples, it will be readily apparent to those of ordinary skill in the art that certain changes and modifications may be made to the teachings of the invention without departing from the spirit or scope of the appended claims.

---

We claim:

1. A stable liquid formulation, comprising: histidine at 40 mM, 3% PEG, 1% glycine, 50 mM arginine, 2% sucrose, and 10-100 mg/ml IL-1 trap that is a dimeric fusion protein comprising the amino acid sequence of SEQ ID NO:10, wherein the formulation has a pH of about 6.5.

2. The stable liquid formulation of claim 1, wherein the PEG is PEG 3350.

3. The stable liquid formulation of claim 1, wherein the IL-1 trap protein is present at about 80 mg/ml.

4. A receptacle containing an amount of the stable liquid formulation of claim 2 extractable as a single dose.

5. The receptacle of claim 4, wherein the single dose has a volume of about 1 ml to about 2 ml.

6. A pre-filled syringe comprising a sterile preparation of a single dose of the stable liquid formulation of claim 2.

7. A stable liquid formulation, comprising: sodium phosphate at 40 mM, 3% PEG, 1% glycine, 50 mM arginine, 2% sucrose, and 10-100 mg/ml IL-1 trap that is a dimeric fusion protein comprising the amino acid sequence of SEQ ID NO:10, wherein the formulation has a pH of about 6.5.

8. The stable liquid formulation of claim 7, wherein the PEG is PEG 3350.

9. The stable liquid formulation of claim 7, wherein the IL-1 trap protein is present at about 80 mg/ml.

10. A receptacle containing an amount of the stable liquid formulation of claim 8 extractable as a single dose.

11. The receptacle of claim 10, wherein the single dose has a volume of about 1 ml to about 2 ml.

12. A pre-filled syringe comprising a sterile preparation of a single dose of the stable liquid formulation of claim 8.

* * * * *

SEQUENCE LISTING

<160> NUMBER OF SEQ ID NOS: 26

<210> SEQ ID NO 1
<211> LENGTH: 2733
<212> TYPE: DNA
<213> ORGANISM: Homo sapiens

<400> SEQUENCE: 1

```
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca agttgcatt tcccttggaa gttgttcaaa agacagctg tttcaattcc      420 cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgccccctg tgatccattc acctaatgat catgtggtct atgagaaaga accaggagag     780
gagctactca ttccctgtac ggtctatttt agttttctga tggattctcg caatgaggtt     840
tggtggacca ttgatggaaa aaaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc caaaggcgaa    1020
gttgccaaag cagccaaggt gaagcagaaa gtgccagctc aagatacac agtgtccggt    1080
```

```
ggcgcgccta tgctgagcga ggctgataaa tgcaaggaac gtgaagaaaa aataatttta    1140
gtgtcatctg caaatgaaat tgatgttcgt ccctgtcctc ttaacccaaa tgaacacaaa    1200
ggcactataa cttggtataa ggatgacagc aagacacctg tatctacaga acaagcctcc    1260
aggattcatc aacacaaaga gaaactttgg tttgttcctg ctaaggtgga ggattcagga    1320
cattactatt gcgtggtaag aaattcatct tactgcctca gaattaaaat aagtgcaaaa    1380
tttgtggaga atgagcctaa cttatgttat aatgcacaag ccatatttaa gcagaaacta    1440
cccgttgcag gagacggagg acttgtgtgc ccttatatgg agttttttaa aaatgaaaat    1500
aatgagttac ctaaattaca gtggtataag gattgcaaac ctctacttct tgacaatata    1560
cactttagtg gagtcaaaga taggctcatc gtgatgaatg tggctgaaaa gcatagaggg    1620
aactatactt gtcatgcatc ctacacatac ttgggcaagc aatatcctat tacccgggta    1680
atagaattta ttactctaga ggaaaacaaa cccacaaggc ctgtgattgt gagcccagct    1740
aatgagacaa tggaagtaga cttgggatcc cagatacaat tgatctgtaa tgtcaccggc    1800
cagttgagtg acattgctta ctggaagtgg aatgggtcag taattgatga agatgaccca    1860
gtgctagggg aagactatta cagtgtggaa atcctgcaa acaaaagaag gagtaccctc    1920
atcacagtgc ttaatatatc ggaaattgag agtagatttt ataaacatcc atttacctgt    1980
tttgccaaga atacacatgg tatagatgca gcatatatcc agttaatata tccagtcact    2040
aattccggag acaaaactca cacatgccca ccgtgcccag cacctgaact cctgggggga    2100
ccgtcagtct tcctcttccc cccaaaaccc aaggacaccc tcatgatctc ccggacccct    2160
gaggtcacat gcgtggtggt ggacgtgagc cacgaagacc ctgaggtcaa gttcaactgg    2220
tacgtggacg gcgtggaggt gcataatgcc aagacaaagc cgcgggagga gcagtacaac    2280
agcacgtacc gtgtggtcag cgtcctcacc gtcctgcacc aggactggct gaatggcaag    2340
gagtacaagt gcaaggtctc caacaaagcc ctcccagccc ccatcgagaa aaccatctcc    2400
aaagccaaag gcagccccg agaaccacag gtgtacaccc tgcccccatc ccgggaggag    2460
atgaccaaga accaggtcag cctgacctgc ctggtcaaag gcttctatcc cagcgacatc    2520
gccgtggagt gggagagcaa tgggcagccg gagaacaact acaagaccac gcctcccgtg    2580
ctggactccg acggctcctt cttcctctat agcaagctca ccgtggacaa gagcaggtgg    2640
cagcagggga acgtcttctc atgctccgtg atgcatgagg ctctgcacaa ccactacacg    2700
cagaagagcc tctccctgtc tccgggtaaa tga                                 2733
```

<210> SEQ ID NO 2
<211> LENGTH: 910
<212> TYPE: PRT
<213> ORGANISM: Homo sapiens

<400> SEQUENCE: 2

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

-continued

```
Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
        355                 360                 365

Asp Lys Cys Lys Glu Arg Glu Glu Lys Ile Ile Leu Val Ser Ser Ala
    370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
            420                 425                 430

Pro Ala Lys Val Glu Asp Ser Gly His Tyr Tyr Cys Val Val Arg Asn
        435                 440                 445

Ser Ser Tyr Cys Leu Arg Ile Lys Ile Ser Ala Lys Phe Val Glu Asn
    450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495
```

-continued

```
Lys Asn Glu Asn Asn Glu Leu Pro Lys Leu Gln Trp Tyr Lys Asp Cys
            500                 505                 510

Lys Pro Leu Leu Leu Asp Asn Ile His Phe Ser Gly Val Lys Asp Arg
            515                 520                 525

Leu Ile Val Met Asn Val Ala Glu Lys His Arg Gly Asn Tyr Thr Cys
            530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
            595                 600                 605

Lys Trp Asn Gly Ser Val Ile Asp Glu Asp Asp Pro Val Leu Gly Glu
            610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
            675                 680                 685

Cys Pro Pro Cys Pro Ala Pro Glu Leu Leu Gly Gly Pro Ser Val Phe
            690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

Lys Phe Asn Trp Tyr Val Asp Gly Val Glu Val His Asn Ala Lys Thr
            740                 745                 750

Lys Pro Arg Glu Glu Gln Tyr Asn Ser Thr Tyr Arg Val Val Ser Val
            755                 760                 765

Leu Thr Val Leu His Gln Asp Trp Leu Asn Gly Lys Glu Tyr Lys Cys
            770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
            820                 825                 830

Lys Gly Phe Tyr Pro Ser Asp Ile Ala Val Glu Trp Glu Ser Asn Gly
            835                 840                 845

Gln Pro Glu Asn Asn Tyr Lys Thr Thr Pro Pro Val Leu Asp Ser Asp
850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910
```

<210> SEQ ID NO 3
<211> LENGTH: 2703
<212> TYPE: DNA
<213> ORGANISM: Homo sapiens

<400> SEQUENCE: 3

| | | | | | |
|---|---|---|---|---|---|
| atggtgttac | tcagacttat | ttgtttcata | gctctactga | tttcttctct | ggaggctgat | 60 |
| aaatgcaagg | aacgtgaaga | aaaaataatt | ttagtgtcat | ctgcaaatga | aattgatgtt | 120 |
| cgtccctgtc | ctcttaaccc | aaatgaacac | aaaggcacta | aacttggta | taaggatgac | 180 |
| agcaagacac | ctgtatctac | agaacaagcc | tccaggattc | atcaacacaa | agagaaactt | 240 |
| tggtttgttc | ctgctaaggt | ggaggattca | ggacattact | attgcgtggt | aagaaattca | 300 |
| tcttactgcc | tcagaattaa | aataagtgca | aaatttgtgg | agaatgagcc | taacttatgt | 360 |
| tataatgcac | aagccatatt | taagcagaaa | ctacccgttg | caggagacgg | aggacttgtg | 420 |
| tgcccttata | tggagttttt | taaaaatgaa | aataatgagt | acctaaaatt | acagtggtat | 480 |
| aaggattgca | acctctact | tcttgacaat | atacacttta | gtggagtcaa | agataggctc | 540 |
| atcgtgatga | atgtggctga | aaagcataga | gggaactata | cttgtcatgc | atcctacaca | 600 |
| tacttgggca | agcaatatcc | tattacccgg | gtaatagaat | ttattactct | agaggaaaac | 660 |
| aaacccacaa | ggcctgtgat | tgtgagccca | gctaatgaga | caatggaagt | agacttggga | 720 |
| tcccagatac | aattgatctg | taatgtcacc | ggccagttga | gtgacattgc | ttactggaag | 780 |
| tggaatgggt | cagtaattga | tgaagatgac | ccagtgctag | gggaagacta | ttacagtgtg | 840 |
| gaaaatcctg | caaacaaaag | aaggagtacc | ctcatcacag | tgcttaatat | atcggaaatt | 900 |
| gagagtagat | tttataaaca | tccatttacc | tgttttgcca | gaatacaca | tggtatagat | 960 |
| gcagcatata | tccagttaat | atatccagtc | actaattcag | aacgctgcga | tgactgggga | 1020 |
| ctagacacca | tgaggcaaat | ccaagtgttt | gaagatgagc | cagctcgcat | caagtgccca | 1080 |
| ctcttgaac | acttcttgaa | attcaactac | agcacagccc | attcagctgg | ccttactctg | 1140 |
| atctggtatt | ggactaggca | ggaccgggac | cttgaggagc | caattaactt | ccgcctcccc | 1200 |
| gagaaccgca | ttagtaagga | gaaagatgtg | ctgtggttcc | ggcccactct | cctcaatgac | 1260 |
| actggcaact | ataactgcat | gttaaggaac | actacatatt | gcagcaaagt | tgcatttccc | 1320 |
| ttggaagttg | ttcaaaaaga | cagctgtttc | aatttccccca | tgaaactccc | agtgcataaa | 1380 |
| ctgtatatag | aatatggcat | tcagaggatc | acttgtccaa | atgtagatgg | atattttcct | 1440 |
| tccagtgtca | aaccgactat | cacttggtat | atgggctgtt | ataaaataca | gaatttaat | 1500 |
| aatgtaatac | ccgaaggtat | gaacttgagt | ttcctcattg | ccttaattc | aaataatgga | 1560 |
| aattacacat | gtgttgttac | atatccagaa | aatggacgta | cgtttcatct | caccaggact | 1620 |
| ctgactgtaa | aggtagtagg | ctctccaaaa | aatgcagtgc | ccctgtgat | ccattcacct | 1680 |
| aatgatcatg | tggtctatga | aaagaaacca | ggagaggagc | tactcattcc | ctgtacggtc | 1740 |
| tattttagtt | ttctgatgga | ttctcgcaat | gaggtttggt | ggaccattga | tggaaaaaaa | 1800 |
| cctgatgaca | tcactattga | tgtcaccatt | aacgaaagta | taagtcatag | tagaacagaa | 1860 |
| gatgaaacaa | gaactcagat | tttgagcatc | aagaaagtta | cctctgagga | tctcaagcgc | 1920 |
| agctatgtct | gtcatgctag | aagtgccaaa | ggcgaagttg | ccaaagcagc | caaggtgaag | 1980 |
| cagaaagtgc | cagctccaag | atacacagtg | gaatccggag | acaaaactca | cacatgccca | 2040 |
| ccgtgcccag | cacctgaact | cctgggggga | ccgtcagtct | tcctcttccc | cccaaaaccc | 2100 |
| aaggacaccc | tcatgatctc | ccggacccct | gaggtcacat | gcgtggtggt | ggacgtgagc | 2160 |

```
cacgaagacc ctgaggtcaa gttcaactgg tacgtggacg gcgtggaggt gcataatgcc    2220
aagacaaagc cgcgggagga gcagtacaac agcacgtacc gtgtggtcag cgtcctcacc    2280
gtcctgcacc aggactggct gaatggcaag gagtacaagt gcaaggtctc caacaaagcc    2340
ctcccagccc ccatcgagaa aaccatctcc aaagccaaag ggcagccccg agaaccacag    2400
gtgtacaccc tgcccccatc ccgggaggag atgaccaaga accaggtcag cctgacctgc    2460
ctggtcaaag gcttctatcc cagcgacatc gccgtggagt gggagagcaa tgggcagccg    2520
gagaacaact acaagaccac gcctcccgtg ctggactccg acggctcctt cttcctctat    2580
agcaagctca ccgtggacaa gagcaggtgg cagcagggga acgtcttctc atgctccgtg    2640
atgcatgagg ctctgcacaa ccactacacg cagaagagcc tctccctgtc tccgggtaaa    2700
tga                                                                 2703
```

<210> SEQ ID NO 4
<211> LENGTH: 900
<212> TYPE: PRT
<213> ORGANISM: Homo sapiens

<400> SEQUENCE: 4

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Pro Val
            260                 265                 270
```

```
Leu Gly Glu Asp Tyr Tyr Ser Val Glu Asn Pro Ala Asn Lys Arg Arg
            275                 280                 285

Ser Thr Leu Ile Thr Val Leu Asn Ile Ser Glu Ile Glu Ser Arg Phe
            290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
            355                 360                 365

Asn Tyr Ser Thr Ala His Ser Ala Gly Leu Thr Leu Ile Trp Tyr Trp
            370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
            435                 440                 445

Cys Phe Asn Ser Pro Met Lys Leu Pro Val His Lys Leu Tyr Ile Glu
450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
            515                 520                 525

Pro Glu Asn Gly Arg Thr Phe His Leu Thr Arg Thr Leu Thr Val Lys
530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
            595                 600                 605

Thr Ile Asn Glu Ser Ile Ser His Ser Arg Thr Glu Asp Glu Thr Arg
610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Asp Lys Thr His Thr Cys Pro Pro Cys Pro Ala Pro Glu Leu Leu
            675                 680                 685

Gly Gly Pro Ser Val Phe Leu Phe Pro Pro Lys Pro Lys Asp Thr Leu
```

```
                690               695              700
Met Ile Ser Arg Thr Pro Glu Val Thr Cys Val Val Asp Val Ser
705                 710                715                720

His Glu Asp Pro Glu Val Lys Phe Asn Trp Tyr Val Asp Gly Val Glu
                725                 730                735

Val His Asn Ala Lys Thr Lys Pro Arg Glu Glu Gln Tyr Asn Ser Thr
                740                 745                 750

Tyr Arg Val Val Ser Val Leu Thr Val Leu His Gln Asp Trp Leu Asn
                755                 760                 765

Gly Lys Glu Tyr Lys Cys Lys Val Ser Asn Lys Ala Leu Pro Ala Pro
770                 775                 780

Ile Glu Lys Thr Ile Ser Lys Ala Lys Gly Gln Pro Arg Glu Pro Gln
785                 790                 795                800

Val Tyr Thr Leu Pro Pro Ser Arg Glu Glu Met Thr Lys Asn Gln Val
                805                 810                 815

Ser Leu Thr Cys Leu Val Lys Gly Phe Tyr Pro Ser Asp Ile Ala Val
                820                 825                 830

Glu Trp Glu Ser Asn Gly Gln Pro Glu Asn Asn Tyr Lys Thr Thr Pro
                835                 840                 845

Pro Val Leu Asp Ser Asp Gly Ser Phe Phe Leu Tyr Ser Lys Leu Thr
850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900

<210> SEQ ID NO 5
<211> LENGTH: 2709
<212> TYPE: DNA
<213> ORGANISM: Homo sapiens

<400> SEQUENCE: 5
atggtgttac tcagacttat ttgtttcata gctctactga tttcttctct ggaggctgat      60
aaatgcaagg aacgtgaaga aaaataatt ttagtgtcat ctgcaaatga atttgatgtt     120
cgtccctgtc ctcttaaccc aaatgaacac aaaggcacta aacttggta taaggatgac     180 agcaagacac tgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa aataatgagt acctaaaatt acagtggtat     480
aaggattgca aacctctact tcttgacaat atacactta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag ggaagactta ttacagtgtg     840
gaaaatcctg caaacaaaag aaggagtacc ctcatcacag tgcttaatat atcggaaatt     900
```

-continued

```
gagagtagat tttataaaca tccatttacc tgttttgcca agaatacaca tggtatagat      960
gcagcatata tccagttaat atatccagtc actaattcag aacgctgcga tgactgggga     1020
ctagacacca tgaggcaaat ccaagtgttt gaagatgagc cagctcgcat caagtgccca     1080
ctctttgaac acttcttgaa attcaactac agcacagccc attcagctgg ccttactctg     1140
atctggtatt ggactaggca ggaccgggac cttgaggagc caattaactt ccgcctcccc     1200
gagaaccgca ttagtaagga gaaagatgtg ctgtggttcc ggcccactct cctcaatgac     1260
actggcaact ataccctgca tgttaaggaac actacatatt gcagcaaagt tgcatttccc     1320
ttggaagttg ttcaaaaaga cagctgtttc aattccccca tgaaactccc agtgcataaa     1380
ctgtatatag aatatggcat tcagaggatc acttgtccaa atgtagatgg atattttcct     1440
tccagtgtca aaccgactat cacttggtat atgggctgtt ataaaataca gaattttaat     1500
aatgtaatac ccgaaggtat gaacttgagt ttcctcattg ccttaatttc aaataatgga     1560
aattacacat gtgttgttac atatccagaa atggacgta cgtttcatct caccaggact      1620
ctgactgtaa aggtagtagg ctctccaaaa aatgcagtgc ccctgtgat ccattcacct      1680 aatgatcatg tggtctatga gaaagaacca ggagaggagc tactcattcc ctgtacggtc     1740
tattttagtt ttctgatgga ttctcgcaat gaggtttggt ggaccattga tggaaaaaaa     1800
cctgatgaca tcactattga tgtcaccatt aacgaaagta taagtcatag tagaacagaa     1860
gatgaaacaa gaactcagat tttgagcatc aagaaagtta cctctgagga tctcaagcgc     1920
agctatgtct gtcatgctag aagtgccaaa ggcgaagttg ccaaagcagc caaggtgaag     1980
cagaaagtgc cagctccaag atacacagtg gaatccggag agtccaaata cggtccgcca     2040
tgcccatcat gcccagcacc tgagttcctg ggggaccat cagtcttcct gttccccca      2100 aaacccaagg acactctcat gatctcccgg acccctgagg tcacgtgcgt ggtggtggac     2160
gtgagccagg aagaccccga ggtccagttc aactggtacg tggatggcgt ggaggtgcat     2220
aatgccaaga caaagccgcg ggaggagcag ttcaacagca cgtaccgtgt ggtcagcgtc     2280
ctcaccgtcc tgcaccagga ctggctgaac ggcaaggagt acaagtgcaa ggtctccaac     2340
aaaggcctcc cgtcctccat cgagaaaacc atctccaaag ccaaagggca gccccgagag     2400
ccacaggtgt acaccctgcc cccatcccag gaggagatga ccaagaacca ggtcagcctg     2460
acctgcctgg tcaaaggctt ctaccccagc gacatcgccg tggagtggga gagcaatggg     2520
cagccggaga caactacaa gaccacgcct cccgtgctgg actccgacgg ctccttcttc      2580
ctctacagca ggctaaccgt ggacaagagc aggtggcagg aggggaatgt cttctcatgc     2640
tccgtgatgc atgaggctct gcacaaccac tacacacaga gagcctctc cctgtctctg      2700 ggtaaatga                                                             2709
```

<210> SEQ ID NO 6
<211> LENGTH: 902
<212> TYPE: PRT
<213> ORGANISM: Homo sapiens

<400> SEQUENCE: 6

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45
```

-continued

```
Glu His Lys Gly Thr Ile Thr Trp Tyr Lys Asp Asp Ser Lys Thr Pro
 50                  55                  60

Val Ser Thr Glu Gln Ala Ser Arg Ile His Gln His Lys Glu Lys Leu
 65                  70                  75                  80

Trp Phe Val Pro Ala Lys Val Glu Asp Ser Gly His Tyr Tyr Cys Val
                 85                  90                  95

Val Arg Asn Ser Ser Tyr Cys Leu Arg Ile Lys Ile Ser Ala Lys Phe
                100                 105                 110

Val Glu Asn Glu Pro Asn Leu Cys Tyr Asn Ala Gln Ala Ile Phe Lys
            115                 120                 125

Gln Lys Leu Pro Val Ala Gly Asp Gly Leu Val Cys Pro Tyr Met
        130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
                180                 185                 190

Tyr Thr Cys His Ala Ser Tyr Thr Tyr Leu Gly Lys Gln Tyr Pro Ile
                195                 200                 205

Thr Arg Val Ile Glu Phe Ile Thr Leu Glu Glu Asn Lys Pro Thr Arg
        210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                    245                 250                 255

Ala Tyr Trp Lys Trp Asn Gly Ser Val Ile Asp Glu Asp Pro Val
                260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
                340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
                420                 425                 430

Tyr Cys Ser Lys Val Ala Phe Pro Leu Glu Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
```

-continued

```
            465                 470                 475                 480
Ser Ser Val Lys Pro Thr Ile Thr Trp Tyr Met Gly Cys Tyr Lys Ile
                    485                 490                 495

Gln Asn Phe Asn Asn Val Ile Pro Glu Gly Met Asn Leu Ser Phe Leu
                500                 505                 510

Ile Ala Leu Ile Ser Asn Asn Gly Asn Tyr Thr Cys Val Val Thr Tyr
            515                 520                 525

Pro Glu Asn Gly Arg Thr Phe His Leu Thr Arg Thr Leu Thr Val Lys
        530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
                580                 585                 590

Trp Trp Thr Ile Asp Gly Lys Lys Pro Asp Asp Ile Thr Ile Asp Val
            595                 600                 605

Thr Ile Asn Glu Ser Ile Ser His Ser Arg Thr Glu Asp Glu Thr Arg
        610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
                660                 665                 670

Gly Glu Ser Lys Tyr Gly Pro Pro Cys Pro Ser Cys Pro Ala Pro Glu
            675                 680                 685

Phe Leu Gly Gly Pro Ser Val Phe Leu Phe Pro Pro Lys Pro Lys Asp
        690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
                740                 745                 750

Ser Thr Tyr Arg Val Val Ser Val Leu Thr Val Leu His Gln Asp Trp
            755                 760                 765

Leu Asn Gly Lys Glu Tyr Lys Cys Lys Val Ser Asn Lys Gly Leu Pro
        770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
                820                 825                 830

Ala Val Glu Trp Glu Ser Asn Gly Gln Pro Glu Asn Asn Tyr Lys Thr
            835                 840                 845

Thr Pro Pro Val Leu Asp Ser Asp Gly Ser Phe Phe Leu Tyr Ser Arg
        850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895
```

Ser Leu Ser Leu Gly Lys
        900

<210> SEQ ID NO 7
<211> LENGTH: 2709
<212> TYPE: DNA
<213> ORGANISM: Homo sapiens

<400> SEQUENCE: 7

```
atggtgttac tcagacttat ttgtttcata gctctactga tttcttctct ggaggctgat      60
aaatgcaagg aacgtgaaga aaaaataatt ttagtgtcat ctgcaaatga aattgatgtt     120
cgtccctgtc ctcttaaccc aaatgaacac aaaggcacta aacttggta aaggatgac      180
agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa aataatgagt acctaaaatt acagtggtat     480
aaggattgca aacctctact tcttgacaat atacactta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag ggaagactta ttacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
gcagcatata tccagttaat atatccagtc actaattcag aacgctgcga tgactgggga    1020
ctagacacca tgaggcaaat ccaagtgttt gaagatgagc cagctcgcat caagtgccca    1080
ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga aaagatgtg ctgtggttcc ggcccactct cctcaatgac    1260
actggcaact ataccgtgcat gttaaggaac actacatatt gcagcaaagt tgcatttccc    1320
ttggaagttg ttcaaaaaga cagctgtttc aattccccca tgaaactccc agtgcataaa    1380
ctgtatatag aatatggcat tcagaggatc acttgtccaa atgtagatgg atatttcct    1440
tccagtgtca aaccgactat cacttggtat atgggctgtt ataaataca gaattttaat    1500
aatgtaatac ccgaaggtat gaacttgagt ttcctcattg ccttaatttc aaataatgga    1560
aattacacat gtgttgttac atatccagaa aatggacgta cgtttcatct caccaggact    1620
ctgactgtaa aggtagtagg ctctccaaaa aatgcagtgc cccctgtgat ccattcacct    1680
aatgatcatg tggtctatga aaagaaacca ggagaggagc tactcattcc ctgtacggtc    1740
tatttttagtt ttctgatgga ttctcgcaat gaggtttggt ggaccattga tggaaaaaaa    1800
cctgatgaca tcactattga tgtcaccatt aacgaaagta aagtcatag tagaacagaa    1860
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaag    1980
cagaaagtgc cagctccaag atacacagtg gaatccggag agtccaaata cggtccgcca    2040
```

```
tgcccaccat gcccagcacc tgagttcctg gggggaccat cagtcttcct gttcccccca    2100
aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga gagcctctcc cctgtctctg    2700
ggtaaatga                                                             2709
```

<210> SEQ ID NO 8
<211> LENGTH: 902
<212> TYPE: PRT
<213> ORGANISM: Homo sapiens

<400> SEQUENCE: 8

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
                20                  25                  30

Ser Ser Ala Asn Glu Ile Asp Val Arg Pro Cys Pro Leu Asn Pro Asn
            35                  40                  45

Glu His Lys Gly Thr Ile Thr Trp Tyr Lys Asp Asp Ser Lys Thr Pro
        50                  55                  60

Val Ser Thr Glu Gln Ala Ser Arg Ile His Gln His Lys Glu Lys Leu
    65                  70                  75                  80

Trp Phe Val Pro Ala Lys Val Glu Asp Ser Gly His Tyr Tyr Cys Val
                    85                  90                  95

Val Arg Asn Ser Ser Tyr Cys Leu Arg Ile Lys Ile Ser Ala Lys Phe
                100                 105                 110

Val Glu Asn Glu Pro Asn Leu Cys Tyr Asn Ala Gln Ala Ile Phe Lys
            115                 120                 125

Gln Lys Leu Pro Val Ala Gly Asp Gly Gly Leu Val Cys Pro Tyr Met
        130                 135                 140

Glu Phe Phe Lys Asn Glu Asn Asn Glu Leu Pro Lys Leu Gln Trp Tyr
    145                 150                 155                 160

Lys Asp Cys Lys Pro Leu Leu Leu Asp Asn Ile His Phe Ser Gly Val
                    165                 170                 175

Lys Asp Arg Leu Ile Val Met Asn Val Ala Glu Lys His Arg Gly Asn
                180                 185                 190

Tyr Thr Cys His Ala Ser Tyr Thr Tyr Leu Gly Lys Gln Tyr Pro Ile
            195                 200                 205

Thr Arg Val Ile Glu Phe Ile Thr Leu Glu Glu Asn Lys Pro Thr Arg
        210                 215                 220

Pro Val Ile Val Ser Pro Ala Asn Glu Thr Met Glu Val Asp Leu Gly
    225                 230                 235                 240

Ser Gln Ile Gln Leu Ile Cys Asn Val Thr Gly Gln Leu Ser Asp Ile
```

-continued

```
            245                 250                 255
Ala Tyr Trp Lys Trp Asn Gly Ser Val Ile Asp Glu Asp Pro Val
            260                 265                 270
Leu Gly Glu Asp Tyr Tyr Ser Val Glu Asn Pro Ala Asn Lys Arg Arg
            275                 280             285
Ser Thr Leu Ile Thr Val Leu Asn Ile Ser Glu Ile Glu Ser Arg Phe
            290                 295                 300
Tyr Lys His Pro Phe Thr Cys Phe Ala Lys Asn Thr His Gly Ile Asp
305                 310                 315                 320
Ala Ala Tyr Ile Gln Leu Ile Tyr Pro Val Thr Asn Ser Glu Arg Cys
                325                 330                 335
Asp Asp Trp Gly Leu Asp Thr Met Arg Gln Ile Gln Val Phe Glu Asp
            340                 345                 350
Glu Pro Ala Arg Ile Lys Cys Pro Leu Phe Glu His Phe Leu Lys Phe
            355                 360                 365
Asn Tyr Ser Thr Ala His Ser Ala Gly Leu Thr Leu Ile Trp Tyr Trp
            370                 375                 380
Thr Arg Gln Asp Arg Asp Leu Glu Glu Pro Ile Asn Phe Arg Leu Pro
385                 390                 395                 400
Glu Asn Arg Ile Ser Lys Glu Lys Asp Val Leu Trp Phe Arg Pro Thr
                405                 410                 415
Leu Leu Asn Asp Thr Gly Asn Tyr Thr Cys Met Leu Arg Asn Thr Thr
            420                 425                 430
Tyr Cys Ser Lys Val Ala Phe Pro Leu Glu Val Val Gln Lys Asp Ser
            435                 440                 445
Cys Phe Asn Ser Pro Met Lys Leu Pro Val His Lys Leu Tyr Ile Glu
            450                 455                 460
Tyr Gly Ile Gln Arg Ile Thr Cys Pro Asn Val Asp Gly Tyr Phe Pro
465                 470                 475                 480
Ser Ser Val Lys Pro Thr Ile Thr Trp Tyr Met Gly Cys Tyr Lys Ile
                485                 490                 495
Gln Asn Phe Asn Asn Val Ile Pro Glu Gly Met Asn Leu Ser Phe Leu
            500                 505                 510
Ile Ala Leu Ile Ser Asn Asn Gly Asn Tyr Thr Cys Val Val Thr Tyr
            515                 520                 525
Pro Glu Asn Gly Arg Thr Phe His Leu Thr Arg Thr Leu Thr Val Lys
            530                 535                 540
Val Val Gly Ser Pro Lys Asn Ala Val Pro Pro Val Ile His Ser Pro
545                 550                 555                 560
Asn Asp His Val Val Tyr Glu Lys Glu Pro Gly Glu Glu Leu Leu Ile
                565                 570                 575
Pro Cys Thr Val Tyr Phe Ser Phe Leu Met Asp Ser Arg Asn Glu Val
            580                 585                 590
Trp Trp Thr Ile Asp Gly Lys Lys Pro Asp Asp Ile Thr Ile Asp Val
            595                 600                 605
Thr Ile Asn Glu Ser Ile Ser His Ser Arg Thr Glu Asp Glu Thr Arg
            610                 615                 620
Thr Gln Ile Leu Ser Ile Lys Lys Val Thr Ser Glu Asp Leu Lys Arg
625                 630                 635                 640
Ser Tyr Val Cys His Ala Arg Ser Ala Lys Gly Glu Val Ala Lys Ala
                645                 650                 655
Ala Lys Val Lys Gln Lys Val Pro Ala Pro Arg Tyr Thr Val Glu Ser
            660                 665                 670
```

-continued

```
Gly Glu Ser Lys Tyr Gly Pro Pro Cys Pro Cys Pro Ala Pro Glu
            675                 680                 685

Phe Leu Gly Gly Pro Ser Val Phe Leu Phe Pro Pro Lys Pro Lys Asp
        690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 9
<211> LENGTH: 2703
<212> TYPE: DNA
<213> ORGANISM: Homo sapiens

<400> SEQUENCE: 9
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta gcaggaccg ggaccttgag      240 gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca agttgcatt tcccttggaa gttgttcaaa agacagctg tttcaattcc       420 ccatgaaac tcccagtgca taaactgtat atagaatatg cattcagag atcacttgt        480 ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
```

-continued

```
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc aagatacac agtggaaaaa   1080
tgcaaggaac gtgaagaaaa ataattttta gtgagctcag caaatgaaat cgatgttcgt   1140
ccctgtcctc ttaacccaaa tgaacacaaa ggcactataa cttggtataa ggatgacagc   1200
aagacacctg tatctacaga acaagcctcc aggattcatc aacacaaaga gaaactttgg   1260
tttgttcctg ctaaggtgga ggattcagga cattactatt gcgtggtaag aaattcatct   1320
tactgcctca gaattaaaat aagtgcaaaa tttgtggaga tgagcctaa cttatgttat   1380
aatgcacaag ccatatttaa gcagaaacta cccgttgcag gagacggagg acttgtgtgc   1440
ccttatatgg agttttttaa aaatgaaaat aatgagttac ctaaattaca gtggtataag   1500
gattgcaaac ctctacttct tgacaatata cactttagtg gagtcaaaga taggctcatc   1560
gtgatgaatg tggctgaaaa gcatagaggg aactatactt gtcatgcatc ctacacatac   1620
ttgggcaagc aatatcctat tacccgggta atagaattta ttactctaga ggaaaacaaa   1680
cccacaaggc ctgtgattgt gagcccagct aatgagacaa tggaagtaga cttgggatcc   1740
cagatacaat tgatctgtaa tgtcaccggc cagttgagtg acattgctta ctggaagtgg   1800
aatgggtcag taattgatga agatgaccca gtgctagggg aagactatta cagtgtggaa   1860
aatcctgcaa acaaaagaag gagtacccctc atcacagtgc ttaatatatc ggaaattgag   1920
agtagatttt ataaacatcc atttacctgt tttgccaaga atacatgg tatagatgca   1980
gcatatatcc agttaatata tccagtcact aattccggag acaaaactca cacatgccca   2040
ccgtgcccag cacctgaact cctgggggga ccgtcagtct tcctcttccc cccaaaaccc   2100
aaggacaccc tcatgatctc ccggacccct gaggtcacat gcgtggtggt ggacgtgagc   2160
cacgaagacc ctgaggtcaa gttcaactgg tacgtggacg gcgtggaggt gcataatgcc   2220
aagacaaagc cgcgggagga gcagtacaac agcacgtacc gtgtggtcag cgtcctcacc   2280
gtcctgcacc aggactggct gaatggcaag gagtacaagt gcaaggtctc caacaaagcc   2340
ctcccagccc ccatcgagaa aaccatctcc aaagccaaag gcagccccg agaaccacag   2400
gtgtacaccc tgccccatc ccgggatgag ctgaccaaga accaggtcag cctgacctgc   2460
ctggtcaaag gcttctatcc cagcgacatc gccgtggagt gggagagcaa tgggcagccg   2520
gagaacaact acaagaccac gcctcccgtg ctggactccg acggctcctt cttcctctac   2580
agcaagctca ccgtggacaa gagcaggtgg cagcagggga acgtcttctc atgctccgtg   2640
atgcatgagg ctctgcacaa ccactacacg cagaagagcc tctccctgtc tccgggtaaa   2700
tga                                                                 2703
```

<210> SEQ ID NO 10
<211> LENGTH: 900
<212> TYPE: PRT
<213> ORGANISM: Homo sapiens

<400> SEQUENCE: 10

```
Met Val Leu Leu Trp Cys Val Val Ser Leu Tyr Phe Tyr Gly Ile Leu
  1               5                  10                  15

Gln Ser Asp Ala Ser Glu Arg Cys Asp Asp Trp Gly Leu Asp Thr Met
```

-continued

```
                    20                  25                  30
Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
 50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
            130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
            355                 360                 365

Ile Leu Val Ser Ser Ala Asn Glu Ile Asp Val Arg Pro Cys Pro Leu
            370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
            435                 440                 445
```

-continued

```
Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Leu Val Cys
465                 470                 475                 480

Pro Tyr Met Glu Phe Lys Asn Glu Asn Asn Glu Leu Pro Lys Leu
                    485                 490                 495

Gln Trp Tyr Lys Asp Cys Lys Pro Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                    565                 570                 575

Asp Leu Gly Ser Gln Ile Gln Leu Ile Cys Asn Val Thr Gly Gln Leu
                580                 585                 590

Ser Asp Ile Ala Tyr Trp Lys Trp Asn Gly Ser Val Ile Asp Glu Asp
            595                 600                 605

Asp Pro Val Leu Gly Glu Asp Tyr Tyr Ser Val Glu Asn Pro Ala Asn
        610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                    645                 650                 655

Gly Ile Asp Ala Ala Tyr Ile Gln Leu Ile Tyr Pro Val Thr Asn Ser
                660                 665                 670

Gly Asp Lys Thr His Thr Cys Pro Pro Cys Pro Ala Pro Glu Leu Leu
            675                 680                 685

Gly Gly Pro Ser Val Phe Leu Phe Pro Pro Lys Pro Lys Asp Thr Leu
        690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                    725                 730                 735

Val His Asn Ala Lys Thr Lys Pro Arg Glu Glu Gln Tyr Asn Ser Thr
                740                 745                 750

Tyr Arg Val Val Ser Val Leu Thr Val Leu His Gln Asp Trp Leu Asn
            755                 760                 765

Gly Lys Glu Tyr Lys Cys Lys Val Ser Asn Lys Ala Leu Pro Ala Pro
        770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                    805                 810                 815

Ser Leu Thr Cys Leu Val Lys Gly Phe Tyr Pro Ser Asp Ile Ala Val
                820                 825                 830

Glu Trp Glu Ser Asn Gly Gln Pro Glu Asn Asn Tyr Lys Thr Thr Pro
            835                 840                 845

Pro Val Leu Asp Ser Asp Gly Ser Phe Phe Leu Tyr Ser Lys Leu Thr
        850                 855                 860
```

| | | | | | | | | | | | |
|---|---|---|---|---|---|---|---|---|---|---|---|
| Val | Asp | Lys | Ser | Arg | Trp | Gln | Gln | Gly | Asn | Val | Phe Ser Cys Ser Val |
| 865 | | | | 870 | | | | 875 | | | 880 |
| Met | His | Glu | Ala | Leu | His | Asn | His | Tyr | Thr | Gln | Lys Ser Leu Ser Leu |
| | | | | 885 | | | | 890 | | | 895 |
| Ser | Pro | Gly | Lys | | | | | | | | |
| | | | 900 | | | | | | | | |

<210> SEQ ID NO 11
<211> LENGTH: 2709
<212> TYPE: DNA
<213> ORGANISM: Homo sapiens

<400> SEQUENCE: 11

| | | | | | |
|---|---|---|---|---|---|
| atggtgcttc | tgtggtgtgt | agtgagtctc | tacttttatg | gaatcctgca | aagtgatgcc | 60 |
| tcagaacgct | gcgatgactg | gggactagac | accatgaggc | aaatccaagt | gtttgaagat | 120 |
| gagccagctc | gcatcaagtg | cccactcttt | gaacacttct | tgaaattcaa | ctacagcaca | 180 |
| gcccattcag | ctggccttac | tctgatctgg | tattggacta | ggcaggaccg | ggaccttgag | 240 |
| gagccaatta | acttccgcct | ccccgagaac | cgcattagta | aggagaaaga | tgtgctgtgg | 300 |
| ttccggccca | ctctcctcaa | tgacactggc | aactatacct | gcatgttaag | gaacactaca | 360 |
| tattgcagca | aagttgcatt | tcccttggaa | gttgttcaaa | aagacagctg | tttcaattcc | 420 |
| cccatgaaac | tcccagtgca | taaactgtat | atagaatatg | gcattcagag | gatcacttgt | 480 |
| ccaaatgtag | atggatattt | tccttccagt | gtcaaaccga | ctatcacttg | gtatatgggc | 540 |
| tgttataaaa | tacagaattt | taataatgta | atacccgaag | gtatgaactt | gagtttcctc | 600 |
| attgccttaa | tttcaaataa | tggaaattac | acatgtgttg | ttacatatcc | agaaaatgga | 660 |
| cgtacgtttc | atctcaccag | gactctgact | gtaaaggtag | taggctctcc | aaaaaatgca | 720 |
| gtgcccctg | tgatccattc | acctaatgat | catgtggtct | atgagaaaga | accaggagag | 780 |
| gagctactca | ttccctgtac | ggtctatttt | agttttctga | tggattctcg | caatgaggtt | 840 |
| tggtggacca | ttgatggaaa | aaaacctgat | gacatcacta | ttgatgtcac | cattaacgaa | 900 |
| agtataagtc | atagtagaac | agaagatgaa | acaagaactc | agattttgag | catcaagaaa | 960 |
| gttacctctg | aggatctcaa | gcgcagctat | gtctgtcatg | ctagaagtgc | caaaggcgaa | 1020 |
| gttgccaaag | cagccaaggt | gaagcagaaa | gtgccagctc | caagatacac | agtgaaaaa | 1080 |
| tgcaaggaac | gtgaagaaaa | aataattta | gtgagctcag | caaatgaaat | cgatgttcgt | 1140 |
| ccctgtcctc | ttaacccaaa | tgaacacaaa | ggcactataa | cttggtataa | ggatgacagc | 1200 |
| aagacacctg | tatctacaga | acaagcctcc | aggattcatc | aacacaaaga | gaaactttgg | 1260 |
| tttgttcctg | ctaaggtgga | ggattcagga | cattactatt | gcgtggtaag | aaattcatct | 1320 |
| tactgcctca | gaattaaaat | aagtgcaaaa | tttgtggaga | atgagcctaa | cttatgttat | 1380 |
| aatgcacaag | ccatatttaa | gcagaaacta | cccgttgcag | agacggagg | acttgtgtgc | 1440 |
| ccttatatgg | agtttttaa | aaatgaaaat | aatgagttac | ctaaattaca | gtggtataag | 1500 |
| gattgcaaac | tctctacttct | tgacaatata | cactttagtg | gagtcaaaga | taggctcatc | 1560 |
| gtgatgaatg | tggctgaaaa | gcatagaggg | aactatactt | gtcatgcatc | ctacacatac | 1620 |
| ttgggcaagc | aatatcctat | tacccgggta | atagaattta | ttactctaga | ggaaacaaa | 1680 |
| cccacaaggc | ctgtgattgt | gagcccagct | aatgagacaa | tggaagtaga | cttgggatcc | 1740 |
| cagatacaat | tgatctgtaa | tgtcaccggc | cagttgagtg | acattgctta | ctggaagtgg | 1800 |
| aatgggtcag | taattgatga | agatgaccca | gtgctagggg | aagactatta | cagtgtggaa | 1860 |

-continued

```
aatcctgcaa acaaagaag gagtacccts atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag agtccaaata cggtccgcca    2040
tgcccatcat gcccagcacc tgagttcctg gggggaccat cagtcttcct gttcccccca    2100
aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga caactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga gagcctctc cctgtctctg    2700
ggtaaatga                                                            2709
```

```
<210> SEQ ID NO 12
<211> LENGTH: 902
<212> TYPE: PRT
<213> ORGANISM: Homo sapiens

<400> SEQUENCE: 12
```

```
Met Val Leu Leu Trp Cys Val Val Ser Leu Tyr Phe Tyr Gly Ile Leu
  1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220
```

-continued

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
            245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
            325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Lys Ile
            355                 360                 365

Ile Leu Val Ser Ser Ala Asn Glu Ile Asp Val Arg Pro Cys Pro Leu
370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
            405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
            435                 440                 445

Ala Lys Phe Val Glu Asn Glu Pro Asn Leu Cys Tyr Asn Ala Gln Ala
450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
            485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
            515                 520                 525

Arg Gly Asn Tyr Thr Cys His Ala Ser Tyr Thr Tyr Leu Gly Lys Gln
530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
            565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
            595                 600                 605

Asp Pro Val Leu Gly Glu Asp Tyr Tyr Ser Val Glu Asn Pro Ala Asn
            610                 615                 620

Lys Arg Arg Ser Thr Leu Ile Thr Val Leu Asn Ile Ser Glu Ile Glu
625                 630                 635                 640

```
Ser Arg Phe Tyr Lys His Pro Phe Thr Cys Phe Ala Lys Asn Thr His
            645                 650                 655
Gly Ile Asp Ala Ala Tyr Ile Gln Leu Ile Tyr Pro Val Thr Asn Ser
        660                 665                 670
Gly Glu Ser Lys Tyr Gly Pro Pro Cys Pro Ser Cys Pro Ala Pro Glu
    675                 680                 685
Phe Leu Gly Gly Pro Ser Val Phe Leu Phe Pro Pro Lys Pro Lys Asp
690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
                725                 730                 735
Val Glu Val His Asn Ala Lys Thr Lys Pro Arg Glu Glu Gln Phe Asn
            740                 745                 750
Ser Thr Tyr Arg Val Val Ser Val Leu Thr Val Leu His Gln Asp Trp
        755                 760                 765
Leu Asn Gly Lys Glu Tyr Lys Cys Lys Val Ser Asn Lys Gly Leu Pro
    770                 775                 780
Ser Ser Ile Glu Lys Thr Ile Ser Lys Ala Lys Gly Gln Pro Arg Glu
785                 790                 795                 800
Pro Gln Val Tyr Thr Leu Pro Pro Ser Gln Glu Glu Met Thr Lys Asn
                805                 810                 815
Gln Val Ser Leu Thr Cys Leu Val Lys Gly Phe Tyr Pro Ser Asp Ile
            820                 825                 830
Ala Val Glu Trp Glu Ser Asn Gly Gln Pro Glu Asn Asn Tyr Lys Thr
        835                 840                 845
Thr Pro Pro Val Leu Asp Ser Asp Gly Ser Phe Phe Leu Tyr Ser Arg
    850                 855                 860
Leu Thr Val Asp Lys Ser Arg Trp Gln Glu Gly Asn Val Phe Ser Cys
865                 870                 875                 880
Ser Val Met His Glu Ala Leu His Asn His Tyr Thr Gln Lys Ser Leu
                885                 890                 895
Ser Leu Ser Leu Gly Lys
            900

<210> SEQ ID NO 13
<211> LENGTH: 2709
<212> TYPE: DNA
<213> ORGANISM: Homo sapiens

<400> SEQUENCE: 13
atggtgcttc tgtggtgtgt agtgagtctc tacttttatg gaatcctgca aagtgatgcc      60
tcagaacgct gcgatgactg ggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta gcaggaccg ggaccttgag     240 gagccaatta acttccgcct ccccgagaac cgcattagta aggagaaaga tgtgctgtgg     300
ttccggccca ctcctccaa tgacactggc aactatacct gcatgttaag gaacactaca     360
tattgcagca agttgcatt tcccttggaa gttgttcaaa agacagctg tttcaattcc     420 cccatgaaac tcccagtgca taaactgtat atagaatatg cattcagag gatcacttgt     480 ccaaatgtag atggatattt tccttccagt gtcaaaccga ctatcacttg gtatatgggc     540
tgttataaaa tacagaattt taataatgta atacccgaag gtatgaactt gagtttcctc     600
```

```
attgccttaa tttcaaataa tggaaattac acatgtgttg ttacatatcc agaaaatgga    660
cgtacgtttc atctcaccag gactctgact gtaaaggtag taggctctcc aaaaaatgca    720 gtgcccctg tgatccattc acctaatgat catgtggtct atgagaaaga accaggagag     780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc aagatacac agtggaaaaa    1080 tgcaaggaac gtgaagaaaa ataattttta gtgagctcag caaatgaaat cgatgttcgt   1140
ccctgtcctc ttaacccaaa tgaacacaaa ggcactataa cttggtataa ggatgacagc   1200
aagacacctg tatctacaga acaagcctcc aggattcatc aacacaaaga gaaactttgg   1260
tttgttcctg ctaaggtgga ggattcagga cattactatt gcgtggtaag aaattcatct   1320
tactgcctca gaattaaaat aagtgcaaaa tttgtggaga atgagcctaa cttatgttat   1380
aatgcacaag ccatatttaa gcagaaacta cccgttgcag gagacggagg acttgtgtgc   1440
ccttatatgg agttttttaa aaatgaaaat aatgagttac ctaaattaca gtggtataag   1500
gattgcaaac tctacttct tgacaatata cactttagtg gagtcaaaga taggctcatc    1560
gtgatgaatg tggctgaaaa gcatagaggg aactatactt gtcatgcatc ctacacatac   1620
ttgggcaagc aatatcctat tacccgggta atagaattta ttactctaga ggaaaacaaa   1680
cccacaaggc ctgtgattgt gagcccagct aatgagacaa tggaagtaga cttgggatcc   1740
cagatacaat tgatctgtaa tgtcaccggc cagttgagtg acattgctta ctggaagtgg   1800
aatgggtcag taattgatga agatgaccca gtgctagggg aagactatta cagtgtggaa   1860
aatcctgcaa acaaaagaag gagtaccctc atcacagtgc ttaatatatc ggaaattgag   1920
agtagatttt ataaacatcc atttacctgt tttgccaaga atacacatgg tatagatgca   1980
gcatatatcc agttaatata tccagtcact aattccggag agtccaaata cggtccgcca   2040
tgcccaccat gcccagcacc tgagttcctg gggggaccat cagtcttcct gttccccca   2100 aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga caactacaa gaccacgcct cccgtgctgg actccgacgg ctccttcttc    2580
ctctacagca ggctaaccgt ggacaagagc aggtggcagg aggggaatgt cttctcatgc   2640
tccgtgatgc atgaggctct gcacaaccac tacacacaga gagcctctc cctgtctctg    2700 ggtaaatga                                                           2709
```

<210> SEQ ID NO 14
<211> LENGTH: 902
<212> TYPE: PRT
<213> ORGANISM: Homo sapiens

<400> SEQUENCE: 14

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
                100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
        130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
                180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415
```

```
Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
            435                 440                 445

Ala Lys Phe Val Glu Asn Glu Pro Asn Leu Cys Tyr Asn Ala Gln Ala
450                 455                 460

Ile Phe Lys Gln Lys Leu Pro Val Ala Gly Asp Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
            515                 520                 525

Arg Gly Asn Tyr Thr Cys His Ala Ser Tyr Thr Tyr Leu Gly Lys Gln
530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
            595                 600                 605

Asp Pro Val Leu Gly Glu Asp Tyr Tyr Ser Val Glu Asn Pro Ala Asn
            610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
                660                 665                 670

Gly Glu Ser Lys Tyr Gly Pro Pro Cys Pro Pro Cys Pro Ala Pro Glu
            675                 680                 685

Phe Leu Gly Gly Pro Ser Val Phe Leu Phe Pro Pro Lys Pro Lys Asp
            690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
            755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
```

-continued

```
                835                 840                 845
Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 15
<211> LENGTH: 2748
<212> TYPE: DNA
<213> ORGANISM: Homo sapiens

<400> SEQUENCE: 15
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc cccaggtgc cctactggtt gtgggcctct      180
gtcagccccc gcatcaacct gacatggcat aaaaatgact ctgctaggac ggtcccagga     240
gaagaagaga cacggatgtg gcccaggac ggtgctctgt ggcttctgcc agccttgcag      300
gaggactctg gcacctacgt ctgcactact agaaatgctt cttactgtga caaaatgtcc     360
attgagctca gagtttttga gaatacagat gctttcctgc cgttcatctc ataccccgcaa   420 attttaacct tgtcaacctc tggggtatta gtatgccctg acctgagtga attcacccgt     480
gacaaaactg acgtgaagat tcaatggtac aaggattctc ttcttttgga taaagacaat     540
gagaaatttc taagtgtgag ggggaccact cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag gaccattcc tgtgatcatt       720 tcccccctca agaccatatc agcttctctg gggtcaagac tgacaatccc atgtaaggtg     780
tttctgggaa ccggcacacc cttaaccacc atgctgtggt ggacggccaa tgacacccac     840
atagagagcg cctacccggg aggccgcgtg accgaggggc cacgccagga atattcagaa     900 ataatgaga actacattga agtgccattg attttttgatc ctgtcacaag agaggatttg     960
cacatggatt ttaaatgtgt tgtccataat accctgagtt tcagacact acgcaccaca    1020 gtcaaggaag cctcctccac gttctcagaa cgctgcgatg actggggact agacaccatg    1080
aggcaaatcc aagtgtttga agatgagcca ctcgcatca agtgcccact ctttgaacac    1140
ttcttgaaat tcaactacag cacagcccat tcagctggcc ttactctgat ctggtattgg    1200
actaggcagg accgggacct tgaggagcca attaacttcc gcctccccga gaaccgcatt    1260
agtaaggaga aagatgtgct gtggttccgg cccactctcc tcaatgacac tggcaactat    1320
acctgcatgt taggaacac tacatattgc agcaagttg catttcccctt ggaagttgtt    1380 caaaaagaca gctgtttcaa ttcccccatg aaactcccag tgcataaact gtatatagaa    1440
tatggcattc agaggatcac ttgtccaaat gtagatggat attttccttc cagtgtcaaa    1500
ccgactatca cttggtatat gggctgttat aaaatacaga attttaataa tgtaataccc    1560
gaaggtatga acttgagttt cctcattgcc ttaatttcaa ataatggaaa ttacacatgt    1620
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
```

```
gtctatgaga aagaaccagg agaggagcta ctcattccct gtacggtcta ttttagtttt    1800
ctgatggatt ctcgcaatga ggtttggtgg accattgatg gaaaaaaacc tgatgacatc    1860
actattgatg tcaccattaa cgaaagtata agtcatagta gaacagaaga tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagacaaa actcacacat gcccaccgtg cccagcacct    2100
gaactcctgg ggggaccgtc agtcttcctc ttccccccaa aacccaagga caccctcatg    2160
atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
gagaaaacca tctccaaagc caaagggcag ccccgagaac cacaggtgta caccctgccc    2460
ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga               2748

<210> SEQ ID NO 16
<211> LENGTH: 915
<212> TYPE: PRT
<213> ORGANISM: Homo sapiens

<400> SEQUENCE: 16

Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190
```

-continued

```
Leu Val His Asp Val Ala Leu Glu Asp Ala Gly Tyr Tyr Arg Cys Val
            195                 200                 205

Leu Thr Phe Ala His Glu Gly Gln Gln Tyr Asn Ile Thr Arg Ser Ile
            210                 215                 220

Glu Leu Arg Ile Lys Lys Lys Glu Thr Ile Pro Val Ile Ile
225                 230                 235                 240

Ser Pro Leu Lys Thr Ile Ser Ala Ser Leu Gly Ser Arg Leu Thr Ile
                    245                 250                 255

Pro Cys Lys Val Phe Leu Gly Thr Gly Thr Pro Leu Thr Thr Met Leu
                260                 265                 270

Trp Trp Thr Ala Asn Asp Thr His Ile Glu Ser Ala Tyr Pro Gly Gly
            275                 280                 285

Arg Val Thr Glu Gly Pro Arg Gln Glu Tyr Ser Glu Asn Asn Glu Asn
            290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
                340                 345                 350

Asp Asp Trp Gly Leu Asp Thr Met Arg Gln Ile Gln Val Phe Glu Asp
            355                 360                 365

Glu Pro Ala Arg Ile Lys Cys Pro Leu Phe Glu His Phe Leu Lys Phe
            370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
                420                 425                 430

Leu Leu Asn Asp Thr Gly Asn Tyr Thr Cys Met Leu Arg Asn Thr Thr
            435                 440                 445

Tyr Cys Ser Lys Val Ala Phe Pro Leu Glu Val Val Gln Lys Asp Ser
450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
                500                 505                 510

Gln Asn Phe Asn Val Ile Pro Glu Gly Met Asn Leu Ser Phe Leu
            515                 520                 525

Ile Ala Leu Ile Ser Asn Asn Gly Asn Tyr Thr Cys Val Val Thr Tyr
            530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
            595                 600                 605

Trp Trp Thr Ile Asp Gly Lys Lys Pro Asp Asp Ile Thr Ile Asp Val
```

|  | 610 |  |  | 615 |  |  | 620 |  |  |  |

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
            645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915

<210> SEQ ID NO 17
<211> LENGTH: 2754
<212> TYPE: DNA
<213> ORGANISM: Homo sapiens

<400> SEQUENCE: 17
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc ccccaggtgc cctactggtt gtgggcctct     180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360

-continued

```
attgagctca gagtttttga gaatacagat gctttcctgc cgttcatctc atacccgcaa    420
attttaacct tgtcaacctc tggggtatta gtatgccctg acctgagtga attcacccgt    480
gacaaaactg acgtgaagat tcaatggtac aaggattctc ttcttttgga taaagacaat    540
gagaaatttc taagtgtgag ggggaccact cacttactcg tacacgatgt ggccctggaa    600
gatgctggct attaccgctg tgtcctgaca tttgcccatg aaggccagca atacaacatc    660
actaggagta ttgagctacg catcaagaaa aaaaagaag agaccattcc tgtgatcatt     720
tccccctca agaccatatc agcttctctg gggtcaagac tgacaatccc atgtaaggtg    780
tttctgggaa ccggcacacc cttaaccacc atgctgtggt ggacggccaa tgacacccac    840
atagagagcg cctacccggg aggccgcgtg accgaggggc cacgccagga atattcagaa    900
aataatgaga actacattga agtgccattg attttgatc ctgtcacaag agaggatttg     960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga aagatgtgct gtggttccgg cccactctcc tcaatgacac tggcaactat   1320
acctgcatgt taggaacac tacatattgc agcaaagttg catttcccctt ggaagttgtt    1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga atttttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtaagca gaaagtgcca    2040
gctccaagat acacagtgtc cggagagtcc aaatacggtc cgccatgccc atcatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcggggag agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca gagcaggtg gcaggagggg aatgtcttct catgctccgt gatgcatgag    2700
gctctgcaca accactacac acagaagagc ctctcccctgt ctctgggtaa atga         2754
```

<210> SEQ ID NO 18
<211> LENGTH: 917
<212> TYPE: PRT
<213> ORGANISM: Homo sapiens

<400> SEQUENCE: 18

```
Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
```

```
                370             375             380
Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
            435                 440                 445

Tyr Cys Ser Lys Val Ala Phe Pro Leu Glu Val Val Gln Lys Asp Ser
450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
            515                 520                 525

Ile Ala Leu Ile Ser Asn Asn Gly Asn Tyr Thr Cys Val Val Thr Tyr
            530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
            595                 600                 605

Trp Trp Thr Ile Asp Gly Lys Lys Pro Asp Asp Ile Thr Ile Asp Val
            610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
            675                 680                 685

Glu Ser Lys Tyr Gly Pro Pro Cys Pro Ser Cys Pro Ala Pro Glu Phe
690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
            755                 760                 765

Thr Tyr Arg Val Val Ser Val Leu Thr Val Leu His Gln Asp Trp Leu
            770                 775                 780

Asn Gly Lys Glu Tyr Lys Cys Lys Val Ser Asn Lys Gly Leu Pro Ser
785                 790                 795                 800
```

```
Ser Ile Glu Lys Thr Ile Ser Lys Ala Lys Gly Gln Pro Arg Glu Pro
                805                 810                 815
Gln Val Tyr Thr Leu Pro Pro Ser Gln Glu Glu Met Thr Lys Asn Gln
            820                 825                 830
Val Ser Leu Thr Cys Leu Val Lys Gly Phe Tyr Pro Ser Asp Ile Ala
        835                 840                 845
Val Glu Trp Glu Ser Asn Gly Gln Pro Glu Asn Asn Tyr Lys Thr Thr
    850                 855                 860
Pro Pro Val Leu Asp Ser Asp Gly Ser Phe Phe Leu Tyr Ser Arg Leu
865                 870                 875                 880
Thr Val Asp Lys Ser Arg Trp Gln Gln Gly Asn Val Phe Ser Cys Ser
                885                 890                 895
Val Met His Glu Ala Leu His Asn His Tyr Thr Gln Lys Ser Leu Ser
            900                 905                 910
Leu Ser Leu Gly Lys
        915

<210> SEQ ID NO 19
<211> LENGTH: 2754
<212> TYPE: DNA
<213> ORGANISM: Homo sapiens

<400> SEQUENCE: 19
atggtgcgct tgtacgtgtt ggtaatggga gtttctgcct tcaccccttca gcctgcggca    60 cacacagggg ctgccagaag ctgccggttt cgtgggaggc attacaagcg ggagttcagg   120
ctggaagggg agcctgtagc cctgaggtgc ccccaggtgc cctactggtt gtgggcctct   180
gtcagccccc gcatcaacct gacatggcat aaaaatgact ctgctaggac ggtcccagga   240
gaagaagaga cacggatgtg ggcccaggac ggtgctctgt ggcttctgcc agccttgcag   300
gaggactctg gcacctacgt ctgcactact agaaatgctt cttactgtga caaaatgtcc   360
attgagctca gagttttga gaatacagat gctttcctgc cgttcatctc atacccgcaa    420 atttaacct tgtcaacctc tggggtatta gtatgccctg acctgagtga attcaccgt     480 gacaaaactg acgtgaagat tcaatggtac aaggattctc ttcttttgga taaagacaat   540
gagaaatttc taagtgtgag ggggaccact cacttactcg tacacgatgt ggccctggaa   600
gatgctggct attaccgctg tgtcctgaca tttgcccatg aaggccagca atacaacatc   660
actaggagta ttgagctacg catcaagaaa aaaaagaag agaccattcc tgtgatcatt    720
tcccccctca gaccatatc agcttctctg ggtcaagac tgacaatccc atgtaaggtg     780
tttctgggaa ccggcacacc cttaaccacc atgctgtggt ggacggccaa tgacacccac   840
atagagagcg cctacccggg aggccgcgtg accgagggc acgccagga atattcagaa    900 aataatgaga actacattga agtgccattg attttgatc ctgtcacaag agaggatttg    960
cacatggatt ttaaatgtgt tgtccataat accctgagtt ttcagacact acgcaccaca  1020
gtcaaggaag cctcctccac gttctcagaa cgctgcgatg actggggact agacaccatg  1080
aggcaaatcc aagtgtttga agatgagcca gctcgcatca gtgcccact ctttgaacac   1140 ttcttgaaat tcaactacag cacagcccat tcagctggcc ttactctgat ctggtattgg  1200
actaggcagg accgggacct tgaggagcca attaacttcc gcctcccga gaaccgcatt   1260 agtaaggaga aagatgtgct gtggttccgg cccactctcc tcaatgacac tggcaactat  1320
acctgcatgt aaggaacaca tacatattgc agcaaagttg catttccctt ggaagttgtt  1380
```

```
caaaaagaca gctgtttcaa ttcccccatg aaactcccag tgcataaact gtatatagaa    1440
tatggcattc agaggatcac ttgtccaaat gtagatggaa attttccttc cagtgtcaaa    1500
ccgactatca cttggtatat gggctgttat aaaatacaga attttaataa tgtaataccc    1560
gaaggtatga acttgagttt cctcattgcc ttaatttcaa ataatggaaa ttacacatgt    1620
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga aagaaccagg agaggagcta ctcattccct gtacggtcta ttttagtttt    1800
ctgatggatt ctcgcaatga ggtttggtgg accattgatg aaaaaaaacc tgatgacatc    1860
actattgatg tcaccattaa cgaaagtata agtcatagta aacagaagaa tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagagtcc aaatacggtc cgccatgccc accatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc aaagccaaaa gggcagcccc gagagccaca ggtgtacacc    2460
ctgcccccat cccaggagga tgaccaagaa ccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca gagcaggtg gcaggagggg aatgtcttct catgctccgt gatgcatgag    2700
gctctgcaca accactacac acagaagagc ctctccctgt ctctgggtaa atga         2754
```

<210> SEQ ID NO 20
<211> LENGTH: 917
<212> TYPE: PRT
<213> ORGANISM: Homo sapiens

<400> SEQUENCE: 20

```
Met Val Arg Leu Tyr Val Leu Val Met Gly Val Ser Ala Phe Thr Leu
  1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
```

-continued

```
            130                 135                 140
Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
210                 215                 220

Glu Leu Arg Ile Lys Lys Lys Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560
```

```
Val Val Gly Ser Pro Lys Asn Ala Val Pro Val Ile His Ser Pro
                565                 570                 575

Asn Asp His Val Val Tyr Glu Lys Glu Pro Gly Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915

<210> SEQ ID NO 21
<211> LENGTH: 2748
<212> TYPE: DNA
<213> ORGANISM: Homo sapiens

<400> SEQUENCE: 21
atggtgcttc tgtggtgtgt agtgagtctc tacttttatg gaatcctgca aagtgatgcc      60
```

-continued

```
tcagaacgct gcgatgactg gggactagac accatgaggc aaatccaagt gtttgaagat      120
gagccagctc gcatcaagtg cccactcttt gaacacttct tgaaattcaa ctacagcaca      180
gcccattcag ctggccttac tctgatctgg tattggacta gcaggaccg ggaccttgag       240
gagccaatta acttccgcct ccccgagaac cgcattagta aggagaaaga tgtgctgtgg      300
ttccggccca ctctcctcaa tgacactggc aactatacct gcatgttaag gaacactaca     360
tattgcagca aagttgcatt tcccttggaa gttgttcaaa aagacagctg tttcaattcc     420
cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgcccctg tgatccattc acctaatgat catgtggtct atgagaaaga accaggagag      780
gagctactca ttccctgtac ggtctatttt agttttctga tggattctcg caatgaggtt     840
tggtggacca ttgatggaaa aaaacctgat gacatcacta ttgatgtcac cattaacgaa     900
agtataagtc atagtagaac agaagatgaa acaagaactc agattttgag catcaagaaa     960
gttacctctg aggatctcaa gcgcagctat gtctgtcatg ctagaagtgc aaaggcgaa    1020
gttgccaaag cagccaaggt gaagcagaaa gtgccagctc aagatacac agtgcacaca     1080
ggggctgcca gaagctgccg gtttcgtggg aggcattaca agcgggagtt caggctggaa    1140
ggggagcctg tagccctgag gtgccccag gtgccctact ggttgtgggc ctctgtcagc     1200
ccccgcatca acctgacatg gcataaaaat gactctgcta ggacggtccc aggagaagaa    1260
gagacacgga tgtgggccca ggacggtgct ctgtggcttc tgccagcctt gcaggaggac    1320
tctggcaccct acgtctgcac tactagaaat gcttcttact gtgacaaaat gtccattgag    1380
ctcagagttt ttgagaatac agatgctttc ctgccgttca tctcatacc gcaaattta     1440
accttgtcaa cctctgggt attagtatgc cctgacctga gtgaattcac ccgtgacaaa    1500
actgacgtga agattcaatg gtacaaggat tctcttcttt tggataaaga caatgagaaa    1560
tttctaagtg tgaggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaaa gaagagacca ttcctgtgat catttccccc    1740
ctcaagacca tatcagcttc tctggggtca agactgacaa tcccatgtaa ggtgtttctg    1800
ggaaccggca cacccttaac caccatgctg tggtggacgg ccaatgacac ccacatagag    1860
agcgcctacc cgggaggccg cgtgaccgag gggccacgcc aggaatattc agaaaataat    1920
gagaactaca ttgaagtgcc attgattttt gatcctgtca aagagagga tttgcacatg    1980
gattttaaat gtgttgtcca taatccctg agttttcaga cactacgcac cacagtcaag    2040
gaagcctcct ccacgttctc cggagacaaa actcacacat gcccaccgtg cccagcacct    2100
gaactcctgg gggaccgtc agtcttcctc ttccccccaa acccaagga caccctcatg    2160
atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
```

-continued

```
gagaaaacca tctccaaagc caaagggcag ccccgagaac cacaggtgta caccctgccc    2460
ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga                2748
```

<210> SEQ ID NO 22
<211> LENGTH: 915
<212> TYPE: PRT
<213> ORGANISM: Homo sapiens

<400> SEQUENCE: 22

```
Met Val Leu Leu Trp Cys Val Val Ser Leu Tyr Phe Tyr Gly Ile Leu
  1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320
```

-continued

```
Val Thr Ser Glu Asp Leu Lys Arg Ser Tyr Val Cys His Ala Arg Ser
                325                 330                 335
Ala Lys Gly Glu Val Ala Lys Ala Lys Val Lys Gln Lys Val Pro
        340                 345                 350
Ala Pro Arg Tyr Thr Val His Thr Gly Ala Ala Arg Ser Cys Arg Phe
            355                 360                 365
Arg Gly Arg His Tyr Lys Arg Glu Phe Arg Leu Glu Gly Glu Pro Val
        370                 375                 380
Ala Leu Arg Cys Pro Gln Val Pro Tyr Trp Leu Trp Ala Ser Val Ser
385                 390                 395                 400
Pro Arg Ile Asn Leu Thr Trp His Lys Asn Asp Ser Ala Arg Thr Val
                405                 410                 415
Pro Gly Glu Glu Glu Thr Arg Met Trp Ala Gln Asp Gly Ala Leu Trp
            420                 425                 430
Leu Leu Pro Ala Leu Gln Glu Asp Ser Gly Thr Tyr Val Cys Thr Thr
        435                 440                 445
Arg Asn Ala Ser Tyr Cys Asp Lys Met Ser Ile Glu Leu Arg Val Phe
    450                 455                 460
Glu Asn Thr Asp Ala Phe Leu Pro Phe Ile Ser Tyr Pro Gln Ile Leu
465                 470                 475                 480
Thr Leu Ser Thr Ser Gly Val Leu Val Cys Pro Asp Leu Ser Glu Phe
                485                 490                 495
Thr Arg Asp Lys Thr Asp Val Lys Ile Gln Trp Tyr Lys Asp Ser Leu
            500                 505                 510
Leu Leu Asp Lys Asp Asn Glu Lys Phe Leu Ser Val Arg Gly Thr Thr
        515                 520                 525
His Leu Leu Val His Asp Val Ala Leu Glu Asp Ala Gly Tyr Tyr Arg
    530                 535                 540
Cys Val Leu Thr Phe Ala His Glu Gly Gln Gln Tyr Asn Ile Thr Arg
545                 550                 555                 560
Ser Ile Glu Leu Arg Ile Lys Lys Lys Glu Glu Thr Ile Pro Val
                565                 570                 575
Ile Ile Ser Pro Leu Lys Thr Ile Ser Ala Ser Leu Gly Ser Arg Leu
            580                 585                 590
Thr Ile Pro Cys Lys Val Phe Leu Gly Thr Gly Thr Pro Leu Thr Thr
        595                 600                 605
Met Leu Trp Trp Thr Ala Asn Asp Thr His Ile Glu Ser Ala Tyr Pro
    610                 615                 620
Gly Gly Arg Val Thr Glu Gly Pro Arg Gln Glu Tyr Ser Glu Asn Asn
625                 630                 635                 640
Glu Asn Tyr Ile Glu Val Pro Leu Ile Phe Asp Pro Val Thr Arg Glu
                645                 650                 655
Asp Leu His Met Asp Phe Lys Cys Val Val His Asn Thr Leu Ser Phe
            660                 665                 670
Gln Thr Leu Arg Thr Thr Val Lys Glu Ala Ser Ser Thr Phe Ser Gly
        675                 680                 685
Asp Lys Thr His Thr Cys Pro Pro Cys Pro Ala Pro Glu Leu Leu Gly
    690                 695                 700
Gly Pro Ser Val Phe Leu Phe Pro Pro Lys Pro Lys Asp Thr Leu Met
705                 710                 715                 720
Ile Ser Arg Thr Pro Glu Val Thr Cys Val Val Val Asp Val Ser His
                725                 730                 735
```

```
Glu Asp Pro Glu Val Lys Phe Asn Trp Tyr Val Asp Gly Val Glu Val
                740                 745                 750

His Asn Ala Lys Thr Lys Pro Arg Glu Glu Gln Tyr Asn Ser Thr Tyr
            755                 760                 765

Arg Val Val Ser Val Leu Thr Val Leu His Gln Asp Trp Leu Asn Gly
        770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915

<210> SEQ ID NO 23
<211> LENGTH: 2754
<212> TYPE: DNA
<213> ORGANISM: Homo sapiens

<400> SEQUENCE: 23
atggtgcttc tgtggtgtgt agtgagtctc tactttatg gaatcctgca aagtgatgcc      60
tcagaacgct gcgatgactg gggactagac accatgaggc aaatccaagt gtttgaagat    120
gagccagctc gcatcaagtg cccactcttt gaacacttct gaaattcaa ctacagcaca     180 gcccattcag ctggccttac tctgatctgg tattggacta gcaggaccg ggaccttgag     240 gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca agttgcatt tcccttggaa gttgttcaaa agacagctg tttcaattcc      420 cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaacctgat gacatcacta ttgatgtcac cattaacgaa    900
agtataagtc atagtagaac agaagatgaa acaagaactc agattttgag catcaagaaa    960
gttacctctg aggatctcaa cgcagctat gtctgtcatg ctagaagtgc caaggcgaa    1020 gttgccaaag cagccaaggt gaagcagaaa gtgccagctc caagatacac agtgcacaca   1080
```

```
gggctgcca aagctgccg gtttcgtggg aggcattaca agcgggagtt caggctggaa    1140
ggggagcctg tagccctgag gtgccccag gtgccctact ggttgtgggc ctctgtcagc    1200
ccccgcatca acctgacatg gcataaaaat gactctgcta ggacggtccc aggagaagaa    1260
gagacacgga tgtgggccca ggacggtgct ctgtggcttc tgccagcctt gcaggaggac    1320
tctggcacct acgtctgcac tactagaaat gcttcttact gtgacaaaat gtccattgag    1380
ctcagagttt ttgagaatac agatgctttc ctgccgttca tctcataccc gcaaatttta    1440
accttgtcaa cctctggggt attagtatgc cctgacctga gtgaattcac ccgtgacaaa    1500
actgacgtga agattcaatg gtacaaggat tctcttcttt tggataaaga caatgagaaa    1560
tttctaagtg tgaggggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaaa gaagagacca ttcctgtgat catttccccc    1740
ctcaagacca tatcagcttc tctggggtca agactgacaa tcccatgtaa ggtgtttctg    1800
ggaaccggca cacccttaac caccatgctg tggtggacgg ccaatgacac ccacatagag    1860
agcgcctacc cgggaggccg cgtgaccgag gggccacgcc aggaatattc agaaaataat    1920
gagaactaca ttgaagtgcc attgattttt gatcctgtca caagagagga tttgcacatg    1980
gattttaaat gtgttgtcca taatccctg agttttcaga cactacgcac acagtcaag    2040 gaagcctcct ccacgttctc cggagagtcc aaatacggtc cgccatgccc atcatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga            2754

<210> SEQ ID NO 24
<211> LENGTH: 917
<212> TYPE: PRT
<213> ORGANISM: Homo sapiens

<400> SEQUENCE: 24

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80
```

```
Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495
```

-continued

```
Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
            515                 520                 525

His Leu Leu Val His Asp Val Ala Leu Glu Asp Ala Gly Tyr Tyr Arg
            530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
            595                 600                 605

Met Leu Trp Trp Thr Ala Asn Asp Thr His Ile Glu Ser Ala Tyr Pro
            610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
            675                 680                 685

Glu Ser Lys Tyr Gly Pro Pro Cys Pro Ser Cys Pro Ala Pro Glu Phe
            690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
            755                 760                 765

Thr Tyr Arg Val Val Ser Val Leu Thr Val Leu His Gln Asp Trp Leu
            770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
            835                 840                 845

Val Glu Trp Glu Ser Asn Gly Gln Pro Glu Asn Asn Tyr Lys Thr Thr
            850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
```

-continued

915

<210> SEQ ID NO 25
<211> LENGTH: 2754
<212> TYPE: DNA
<213> ORGANISM: Homo sapiens

<400> SEQUENCE: 25

| | |
|---|---|
| atggtgcttc tgtggtgtgt agtgagtctc tactttatg gaatcctgca aagtgatgcc | 60 |
| tcagaacgct gcgatgactg gggactagac accatgaggc aaatccaagt gtttgaagat | 120 |
| gagccagctc gcatcaagtg cccactcttt gaacacttct tgaaattcaa ctacagcaca | 180 |
| gcccattcag ctggccttac tctgatctgg tattggacta ggcaggaccg ggaccttgag | 240 |
| gagccaatta acttccgcct ccccgagaac cgcattagta aggagaaaga tgtgctgtgg | 300 |
| ttccggccca ctctcctcaa tgacactggc aactatacct gcatgttaag aacacactaca | 360 |
| tattgcagca aagttgcatt tcccttggaa gttgttcaaa aagacagctg tttcaattcc | 420 |
| cccatgaaac tcccagtgca taaactgtat atagaatatg gcattcagag gatcacttgt | 480 |
| ccaaatgtag atggatattt tccttccagt gtcaaaccga ctatcacttg gtatatgggc | 540 |
| tgttataaaa tacagaattt taataatgta atacccgaag gtatgaactt gagtttcctc | 600 |
| attgccttaa tttcaaataa tggaaattac acatgtgttg ttacatatcc agaaaatgga | 660 |
| cgtacgtttc atctcaccag gactctgact gtaaaggtag taggctctcc aaaaaatgca | 720 |
| gtgccccctg tgatccattc acctaatgat catgtggtct atgagaaaga accaggagag | 780 |
| gagctactca ttccctgtac ggtctatttt agttttctga tggattctcg caatgaggtt | 840 |
| tggtggacca ttgatggaaa aaaacctgat gacatcacta ttgatgtcac cattaacgaa | 900 |
| agtataagtc atagtagaac agaagatgaa acaagaactc agattttgag catcaagaaa | 960 |
| gttacctctg aggatctcaa gcgcagctat gtctgtcatg ctagaagtgc caaaggcgaa | 1020 |
| gttgccaaag cagccaaggt gaagcagaaa gtgccagctc aagatacac agtgcacaca | 1080 |
| ggggctgcca gaagctgccg gtttcgtggg aggcattaca agcgggagtt caggctggaa | 1140 |
| ggggagcctg tagccctgag gtgcccccag gtgccctact ggttgtgggc ctctgtcagc | 1200 |
| ccccgcatca acctgacatg gcataaaaat gactctgcta ggacggtccc aggagaagaa | 1260 |
| gagacacgga tgtgggccca ggacggtgct ctgtggcttc tgccagcctt gcaggaggac | 1320 |
| tctggcacct acgtctgcac tactagaaat gcttcttact gtgacaaaat gtccattgag | 1380 |
| ctcagagttt ttgagaatac agatgctttc ctgccgttca tctcataccc gcaaattta | 1440 |
| accttgtcaa cctctggggt attagtatgc cctgacctga gtgaattcac ccgtgacaaa | 1500 |
| actgacgtga agattcaatg gtacaaggat tctcttcttt tggataaaga caatgagaaa | 1560 |
| tttctaagtg tgagggggac cactcactta ctcgtacacg atgtggccct ggaagatgct | 1620 |
| ggctattacc gctgtgtcct gacatttgcc catgaaggcc agcaatacaa catcactagg | 1680 |
| agtattgagc tacgcatcaa gaaaaaaaaa gaagagacca ttcctgtgat catttccccc | 1740 |
| ctcaagacca tatcagcttc tctggggtca agactgacaa tcccatgtaa ggtgtttctg | 1800 |
| ggaaccggca caccttaac caccatgctg tggtggacgg ccaatgacac ccacatagag | 1860 |
| agcgcctacc cggaggccg cgtgaccgag gggccacgcc aggaatattc agaaaataat | 1920 |
| gagaactaca ttgaagtgcc attgattttt gatcctgtca agagagga tttgcacatg | 1980 |
| gattttaaat gtgttgtcca taatacctg agttttcaga cactacgcac cacagtcaag | 2040 |
| gaagcctcct ccacgttctc cggagagtcc aaatacggtc cgccatgccc accatgccca | 2100 |

```
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga tgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga          2754
```

<210> SEQ ID NO 26
<211> LENGTH: 917
<212> TYPE: PRT
<213> ORGANISM: Homo sapiens

<400> SEQUENCE: 26

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255
```

-continued

```
Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
```

```
                        -continued
            675               680               685
Glu Ser Lys Tyr Gly Pro Pro Cys Pro Pro Cys Pro Ala Pro Glu Phe
        690             695             700

Leu Gly Gly Pro Ser Val Phe Leu Phe Pro Pro Lys Pro Lys Asp Thr
705             710             715                 720

Leu Met Ile Ser Arg Thr Pro Glu Val Thr Cys Val Val Val Asp Val
            725             730                 735

Ser Gln Glu Asp Pro Glu Val Gln Phe Asn Trp Tyr Val Asp Gly Val
            740             745             750

Glu Val His Asn Ala Lys Thr Lys Pro Arg Glu Glu Gln Phe Asn Ser
        755             760             765

Thr Tyr Arg Val Val Ser Val Leu Thr Val Leu His Gln Asp Trp Leu
        770             775             780

Asn Gly Lys Glu Tyr Lys Cys Lys Val Ser Asn Lys Gly Leu Pro Ser
785             790             795             800

Ser Ile Glu Lys Thr Ile Ser Lys Ala Lys Gly Gln Pro Arg Glu Pro
            805             810             815

Gln Val Tyr Thr Leu Pro Pro Ser Gln Glu Glu Met Thr Lys Asn Gln
            820             825             830

Val Ser Leu Thr Cys Leu Val Lys Gly Phe Tyr Pro Ser Asp Ile Ala
            835             840             845

Val Glu Trp Glu Ser Asn Gly Gln Pro Glu Asn Asn Tyr Lys Thr Thr
        850             855             860

Pro Pro Val Leu Asp Ser Asp Gly Ser Phe Phe Leu Tyr Ser Arg Leu
865             870             875             880

Thr Val Asp Lys Ser Arg Trp Gln Glu Gly Asn Val Phe Ser Cys Ser
            885             890             895

Val Met His Glu Ala Leu His Asn His Tyr Thr Gln Lys Ser Leu Ser
            900             905             910

Leu Ser Leu Gly Lys
            915
```